US010251748B2

United States Patent
Ciobanu et al.

(10) Patent No.: US 10,251,748 B2
(45) Date of Patent: Apr. 9, 2019

(54) CENTERING DEVICES FOR USE WITH A VALVE PROSTHESIS DELIVERY SYSTEM AND METHODS OF USE THEREOF

(71) Applicant: Medtronic Vascular, Inc., Santa Rosa, CA (US)

(72) Inventors: Constantin Ciobanu, Ballybrit (IE); Niall Duffy, Ballybrit (IE); Frank White, Ballybrit (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 244 days.

(21) Appl. No.: 15/000,558

(22) Filed: Jan. 19, 2016

(65) Prior Publication Data

US 2016/0235531 A1    Aug. 18, 2016

Related U.S. Application Data

(60) Provisional application No. 62/115,473, filed on Feb. 12, 2015.

(51) Int. Cl.
*A61F 2/24* (2006.01)

(52) U.S. Cl.
CPC .......... *A61F 2/2427* (2013.01); *A61F 2/2436* (2013.01)

(58) Field of Classification Search
CPC ...... A61F 2/2427; A61F 2/2436; A61F 2/243; A61F 2/2433; A61F 2/82; A61F 2/958
See application file for complete search history.

(56) References Cited

U.S. PATENT DOCUMENTS

| 4,909,252 | A  | 3/1990  | Goldberger    |
| 5,840,067 | A  | 11/1998 | Berguer et al.|
| 6,629,534 | B1 | 10/2003 | St. Goar et al.|
| 8,142,492 | B2 | 3/2012  | Forster et al.|
| 8,454,686 | B2 | 6/2013  | Alkhatib      |
| 8,715,337 | B2 | 5/2014  | Chuter        |
| 8,961,595 | B2 | 2/2015  | Alkhatib      |

(Continued)

OTHER PUBLICATIONS

PCT/US2016/015157, The International Search Report and the Written Onion of the International Searching Authority, dated Apr. 26, 2016.

*Primary Examiner* — Todd J Scherbel
*Assistant Examiner* — Brooke Labranche
(74) *Attorney, Agent, or Firm* — Medler Ferro Woodhouse & Mills PLLC

(57) ABSTRACT

Embodiments hereof relate to centering devices for use with a valve delivery system and methods of delivering a valve prosthesis within a vasculature. A valve centering catheter is configured for use with a valve delivery system. The valve centering catheter includes a circumferential centering device at a distal portion thereof, and the circumferential centering device defines a central opening there-through when in an expanded configuration. The circumferential centering device is annular or has a C-shaped cross-section. The valve delivery system is tracked through the vasculature until the valve prosthesis is positioned through the central opening of the expanded circumferential centering device. The valve centering catheter may alternatively include a longitudinal centering device which acts as a marker for depth control during delivery of a valve delivery system, which may include an integral circumferential centering device.

20 Claims, 19 Drawing Sheets

(56) References Cited

U.S. PATENT DOCUMENTS

| | | | |
|---|---|---|---|
| 9,017,399 B2* | 4/2015 | Gross | A61B 17/068 623/2.1 |
| 9,603,705 B2 | 3/2017 | Alkhatib | |
| 2004/0003819 A1 | 1/2004 | St. Goar et al. | |
| 2004/0225354 A1* | 11/2004 | Allen | A61F 2/2412 623/2.11 |
| 2007/0088431 A1 | 4/2007 | Bourang et al. | |
| 2008/0009746 A1 | 1/2008 | Forster et al. | |
| 2008/0147160 A1 | 6/2008 | Ghione et al. | |
| 2008/0221384 A1 | 9/2008 | Chi Sing et al. | |
| 2010/0249915 A1 | 9/2010 | Zhang | |
| 2010/0280589 A1 | 11/2010 | Styrc | |
| 2011/0245911 A1 | 10/2011 | Quill et al. | |
| 2011/0245917 A1 | 10/2011 | Savage et al. | |
| 2011/0251675 A1 | 10/2011 | Dwork et al. | |
| 2011/0251681 A1 | 10/2011 | Shipley et al. | |
| 2011/0251682 A1 | 10/2011 | Murray, III | |
| 2011/0264200 A1 | 10/2011 | Tran et al. | |
| 2011/0264202 A1 | 10/2011 | Murray, III | |
| 2012/0209375 A1 | 8/2012 | Madrid et al. | |
| 2013/0304200 A1 | 11/2013 | McLean et al. | |
| 2013/0325101 A1 | 12/2013 | Goetz et al. | |
| 2013/0331929 A1* | 12/2013 | Mitra | A61L 31/145 623/2.11 |
| 2014/0018912 A1 | 1/2014 | Delaloye et al. | |
| 2014/0194981 A1 | 7/2014 | Menk et al. | |
| 2014/0257248 A1 | 9/2014 | Millett | |
| 2015/0209136 A1 | 7/2015 | Braido et al. | |
| 2017/0189180 A1 | 7/2017 | Alkhatib | |
| 2017/0189181 A1 | 7/2017 | Alkhatib et al. | |
| 2017/0209261 A1 | 7/2017 | Bortlein et al. | |
| 2017/0252154 A1 | 9/2017 | Tubishevitz et al. | |
| 2017/0290661 A1 | 10/2017 | Von Segesser et al. | |
| 2017/0340438 A1 | 11/2017 | Salahieh et al. | |

* cited by examiner

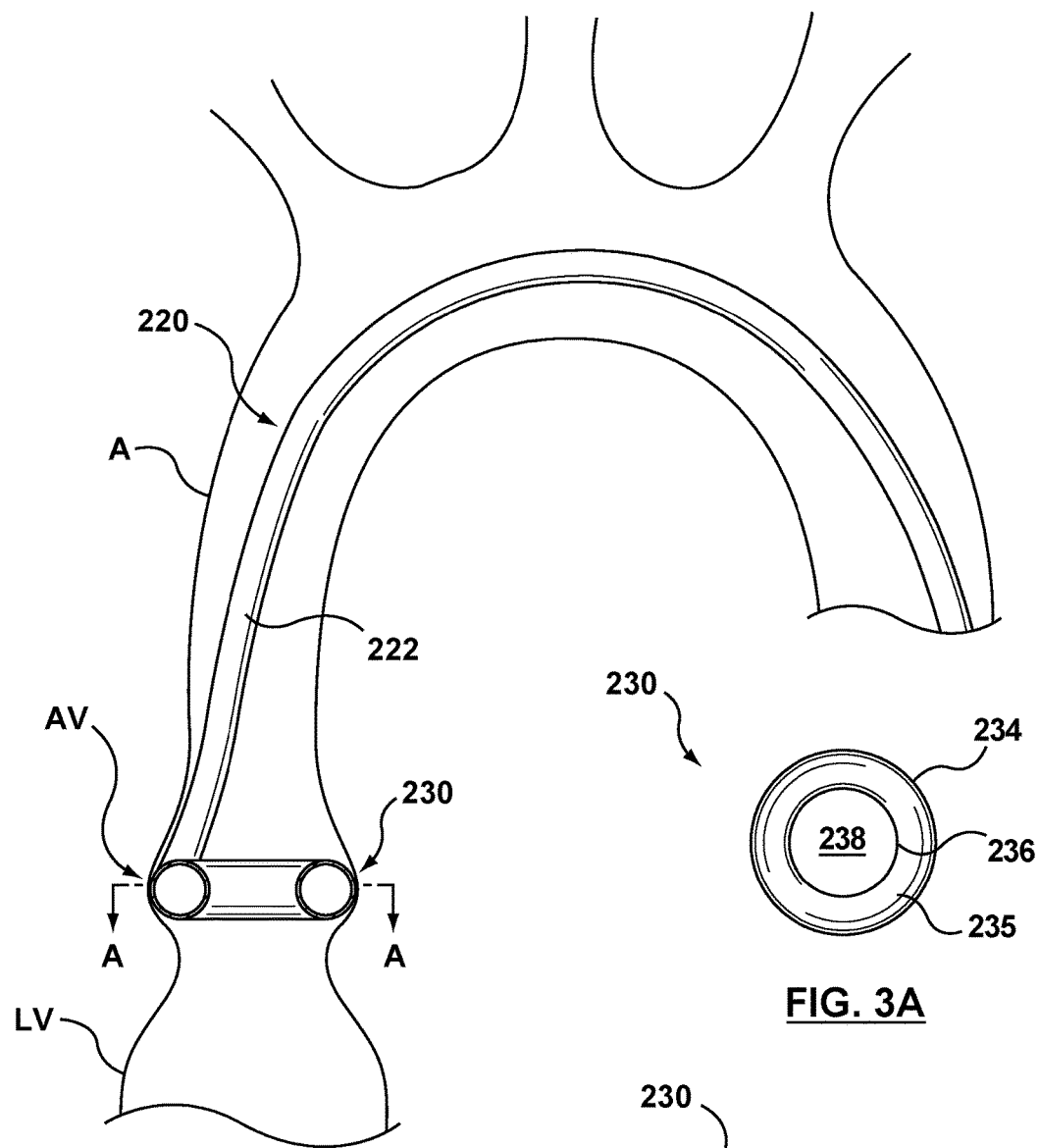
FIG. 3
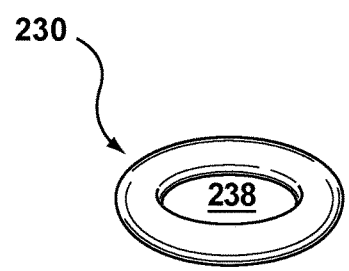
FIG. 3A
FIG. 3B

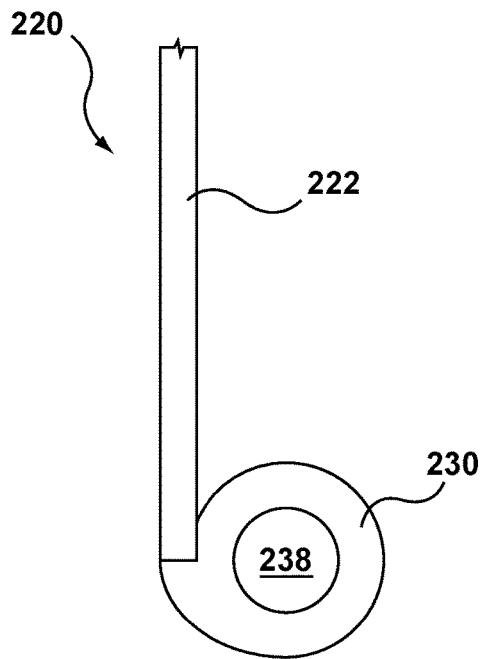
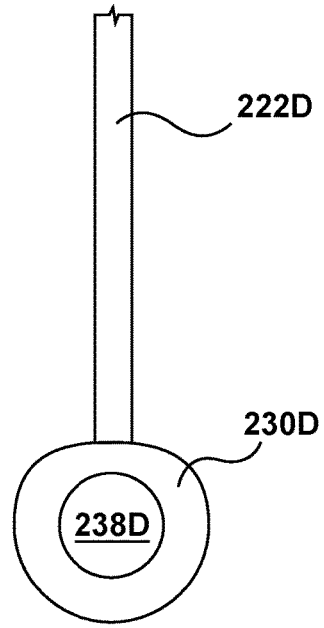
FIG. 3C  FIG. 3D
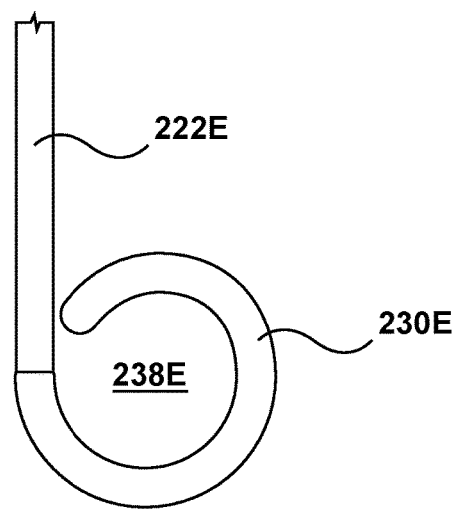
FIG. 3E

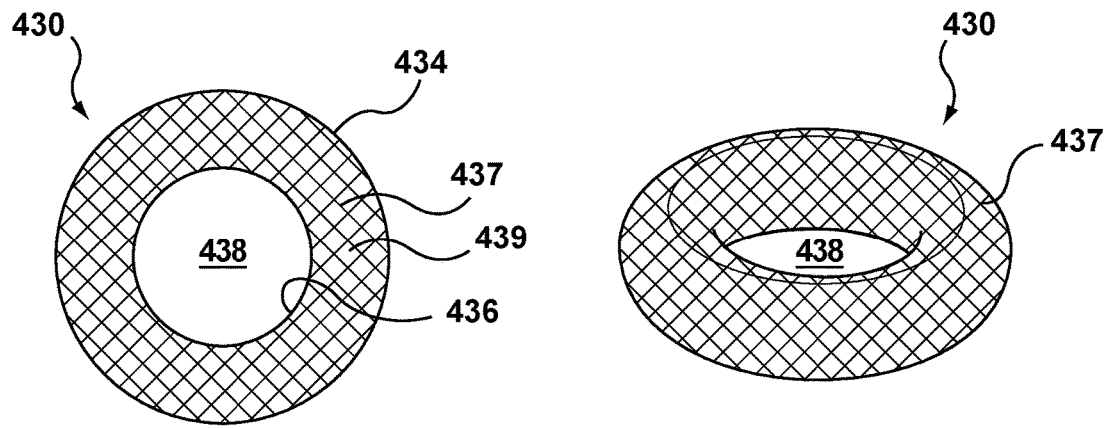
FIG. 4
FIG. 5
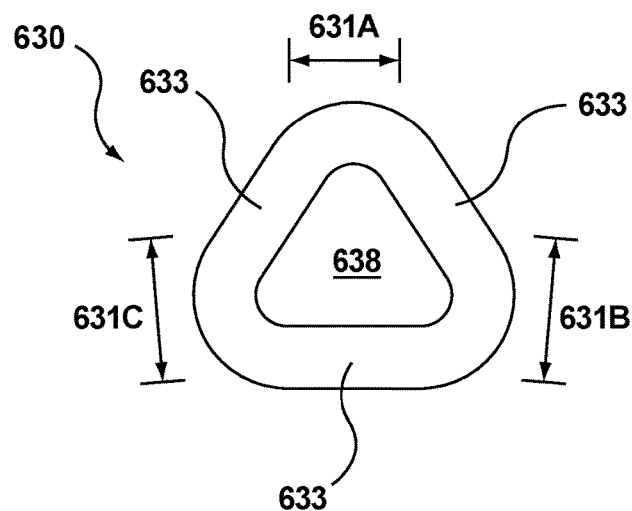
FIG. 6

CENTERING DEVICES FOR USE WITH A VALVE PROSTHESIS DELIVERY SYSTEM AND METHODS OF USE THEREOF

CROSS-REFERENCE TO RELATED APPLICATIONS

This application claims the benefit of U.S. Provisional Patent Application Ser. No. 62/115,473, filed Feb. 12, 2015, which is hereby incorporated by reference in its entirety for all purposes.

FIELD OF THE INVENTION

The invention relates to valve prostheses and more particularly to centering devices configured for use with a valve delivery system for positioning a valve prosthesis in situ.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent or scaffold structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by compressing onto a balloon catheter or by being contained within a sheath component of a delivery system, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Pat. No. 8,721,713, both filed by Tower et al., each of which is incorporated by reference herein in its entirety.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the valve prosthesis, conduction disturbances, coronary artery obstruction, and/or undesirable paravalvular leakage and/or regurgitation at the implantation site. More particularly, for example, if a prosthesis is not longitudinally centered relative to the native annulus, i.e., a prosthesis is positioned too deep or too shallow relative to the native annulus or is placed unevenly within the native annulus in terms of depth, the deployed prosthesis may cause conduction disturbances. In another example, if a prosthesis is not circumferentially centered relative to the native annulus, the deployed prosthesis may dislodge from the implantation site and/or undesirable paravalvular leakage and/or regurgitation may occur. Thus, it is imperative that the prosthesis be accurately positioned relative to the native annulus prior to full deployment of the prosthesis.

Embodiments hereof are directed to centering devices for use with a delivery system for a transcatheter valve prosthesis to address one or more of the afore-mentioned complications.

BRIEF SUMMARY OF THE INVENTION

Embodiments hereof relate to methods of delivering a valve prosthesis configured for delivery within a vasculature. A valve centering catheter is percutaneously introduced into a vasculature. The valve centering catheter has a circumferential centering device at a distal portion thereof, and the circumferential centering device is in a delivery configuration. The valve centering catheter is tracked through the vasculature until the circumferential centering device is positioned at a treatment site. The circumferential centering device is radially expanded into an expanded configuration at the treatment site. The circumferential centering device defines a central opening there-through when in the expanded configuration. A valve delivery system is percutaneously introduced into the vasculature. The valve delivery system has a valve prosthesis at a distal portion thereof and the valve prosthesis is in a delivery configuration. The valve delivery system is tracked through the vasculature until the valve prosthesis is positioned or extends through the central opening of the expanded circumferential centering device. At least an inflow end of the valve prosthesis is deployed into apposition with the native anatomy of the treatment site, thereby anchoring and securing a circumferentially centered position of the valve prosthesis within the native anatomy of the treatment site.

In another embodiment hereof, a valve centering catheter is percutaneously introduced into a vasculature. The valve centering catheter has a longitudinal centering device at a distal portion thereof and the longitudinal centering device is in a delivery configuration. The valve centering catheter is tracked through the vasculature until the longitudinal centering device is positioned distal to or beyond a treatment site. The longitudinal centering device is radially expanded into an expanded configuration, and the longitudinal centering device defines a central opening there-through when in the expanded configuration. A valve delivery system is percutaneously introduced into the vasculature. The valve delivery system has a valve prosthesis mounted at a distal portion thereof and includes a circumferential centering device proximal to the valve prosthesis. The valve prosthesis and the circumferential centering device are in delivery configurations. The valve delivery system is tracked through the vasculature until the valve prosthesis is positioned at the treatment site, proximal to the expanded longitudinal centering device, in order to longitudinally center the valve prosthesis within the native anatomy of the treatment site. The circumferential centering device of the valve delivery system is radially expanded into an expanded configuration, and the circumferential centering device defines a central opening there-through when in the expanded configuration. The valve prosthesis is deployed into apposition with the native anatomy of the treatment site, thereby anchoring and securing the longitudinally and circumferentially centered position of the valve prosthesis within the native anatomy of the treatment site.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is an illustration of the valve centering catheter of FIG. 2, wherein the circumferential centering device is in a deployed or expanded configuration in situ.

FIG. 3A is a cross-sectional view taken along line A-A of FIG. 3.

FIG. 3B is a perspective view of the circumferential centering device of FIG. 3 removed from the valve centering catheter for illustrative purposes only, wherein the circumferential centering device is in a deployed or expanded configuration.

FIG. 3C is a top view illustration of the valve centering catheter of FIG. 2, wherein the circumferential centering device is sealingly attached to a distal end of an outer shaft so as to be longitudinally offset with the outer shaft.

FIG. 3D is a top view illustration of a valve centering catheter according to another embodiment hereof, wherein the circumferential centering device thereof is sealingly attached to a distal end of an outer shaft so as to be longitudinally aligned with the outer shaft.

FIG. 3E is a top view illustration of a valve centering catheter according to another embodiment hereof, wherein the circumferential centering device thereof is sealingly attached to a distal end of an outer shaft and coils or follows a circular path from the outer shaft in order to define a central opening or lumen.

FIG. 4 is a cross-sectional view of a circumferential centering device according to another embodiment hereof, wherein the circumferential centering device includes a mesh and is shown in a deployed or expanded configuration.

FIG. 5 is a perspective view of the circumferential centering device of FIG. 4, wherein the circumferential centering device is in a deployed or expanded configuration.

FIG. 6 is a cross-sectional view of a circumferential centering device according to another embodiment hereof, wherein the circumferential centering device includes a plurality of deformable portions and is shown in a deployed or expanded configuration.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers.

The following detailed description is merely exemplary in nature and is not intended to limit the invention or the application and uses of the invention. Although the description of embodiments hereof are in the context of delivery systems for delivering a valve prosthesis within a native aortic valve, the centering devices of the invention can also be used in other areas of the body, such as for delivering a valve prosthesis within a native mitral valve, for delivering a valve prosthesis within a native pulmonic valve, for delivering a valve prosthesis within a native tricuspid valve, for delivering a venous valve, or for delivering a valve prosthesis within a failed previously-implanted prosthesis. Furthermore, there is no intention to be bound by any expressed or implied theory presented in the preceding technical field, background, brief summary or the following detailed description.

Figures 1, 1A:
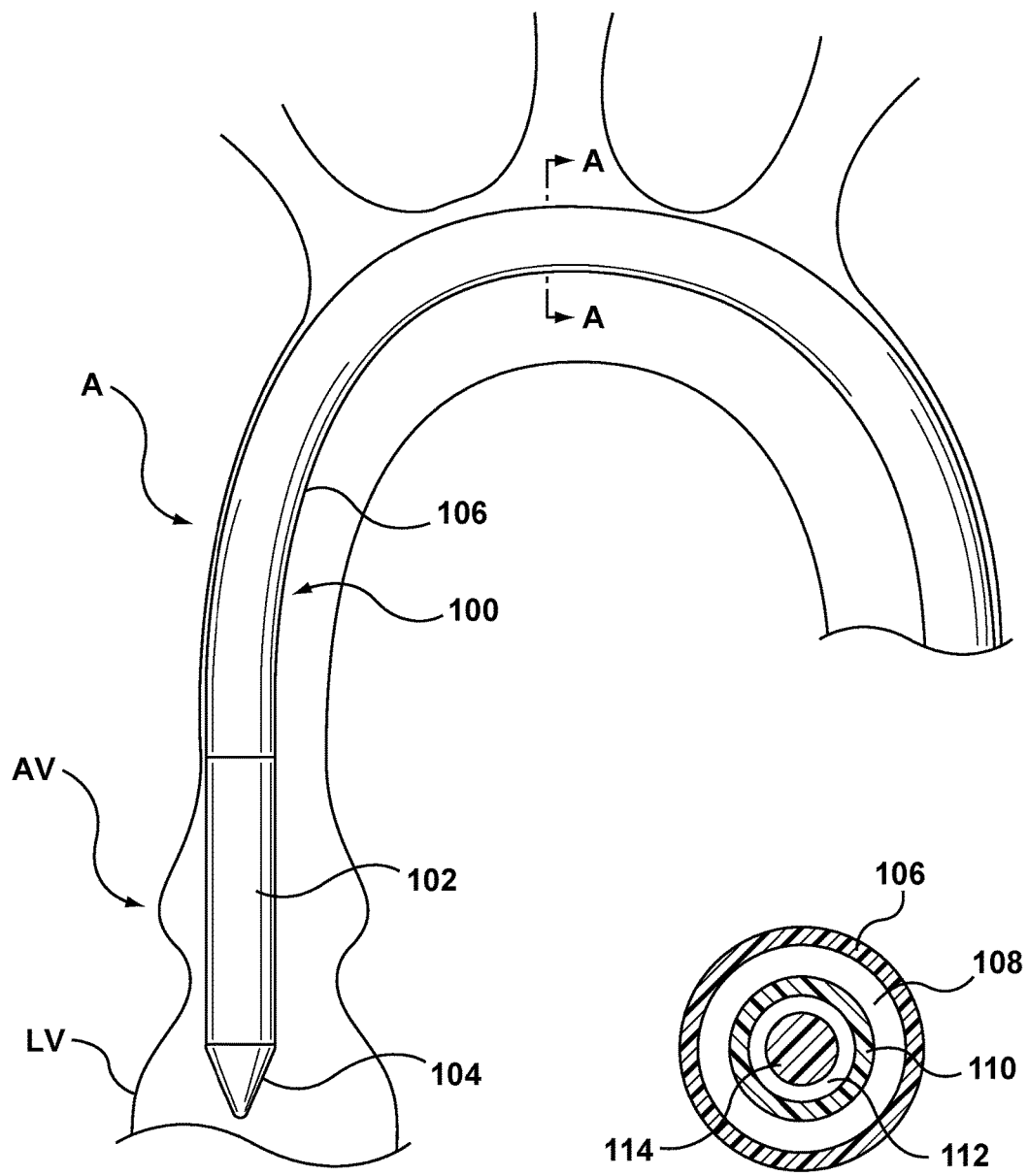
FIG. 1 is an illustration of a valve delivery system in situ.
FIG. 1A is a cross-sectional view taken along line A-A of FIG. 1.

FIGS. 1-1A illustrate a valve delivery system 100 that is configured for endoluminal transcatheter repair/replacement of a defective heart valve. Valve delivery system 100 is depicted in a delivery configuration in FIG. 1 with a valve prosthesis (not shown) loaded within a distal capsule section 102 of the delivery system. As shown in FIG. 1A, valve delivery system 100 also includes a tubular outer shaft 106 defining a lumen 108 there-through and a tubular inner shaft 110 defining a lumen 112 there-through. A distal tip 104 is coupled to a distal end of inner shaft 110. Inner shaft 106 is concentrically disposed within lumen 108 of outer shaft 108, and lumen 112 of inner shaft 110 is sized to slidingly receive a guidewire 114 such that valve delivery system 100 is configured to be tracked over the guidewire during delivery of the valve prosthesis. In the delivery configuration of FIG. 1, distal capsule section 102 is disposed over the valve prosthesis to compressively retain the valve prosthesis in crimped engagement with inner shaft 110. Valve delivery system 100 may be one of, but is not limited to, the delivery systems described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and U.S. Patent Publication No. 2011/0264202 to Murray, III et al., each of which is herein incorporated by reference in its entirety.

Although the valve prosthesis is not shown in FIG. 1, it will be understood by those of ordinary skill in the art that the valve prosthesis includes a stent frame maintaining a valve structure (tissue or synthetic) within the stent frame, the stent frame being biased in its expanded configuration and being collapsible to a compressed delivery arrangement for loading within valve delivery system 100. The stent frame is constructed to self-deploy or self-expand when released from valve delivery system 100. In an embodiment, a valve prosthesis useful with embodiments hereof can be a valve prosthesis as disclosed in U.S. Pat. Appl. Pub. No. 2008/0071361 to Tuval et al., which is incorporated by reference herein in its entirety. Other non-limiting examples of transcatheter valve prostheses useful with systems and methods of the present disclosure are described in U.S. Pat. Appl. Pub. No. 2006/0265056 to Nguyen et al., U.S. Pat. Appl. Pub. No. 2007/0239266 to Birdsall, and U.S. Pat. Appl. Pub. No. 2007/0239269 to Dolan et al., each of which is incorporated by reference herein in its entirety.

As shown in FIG. 1, in accordance with techniques known in the field of interventional cardiology and/or interventional radiology, valve delivery system 100 is transluminally advanced in a retrograde approach through the vasculature to the treatment site, which in this instance is a target diseased native aortic valve AV that extends between a patient's left ventricle LV and a patient's aorta A. Delivery of valve delivery system 100 to the native aortic valve AV is accomplished via a percutaneous transfemoral approach in which the delivery system is tracked through the femoral artery, up the aorta and around the aortic arch in order to access the native aortic valve AV. Delivery system 1010 may also be positioned within the desired area of the heart via different delivery methods known in the art for accessing heart valves. During delivery, the valve prosthesis remains compressed within distal capsule section 102 of the delivery system. Valve delivery system 100 is advanced until distal tip 104 is distal to the native aortic valve AV and disposed within the left ventricle LV as shown in FIG. 1. As valve delivery system 100 is tracked to the native aortic valve AV, the delivery system may abut against or hug the vessel wall as shown in FIG. 1, thereby resulting in a non-circumferentially centered position in the aorta A and in the native aortic valve AV. As described in the background section hereof, proper positioning of the delivery system and valve prosthesis is required in order to successfully implant the valve prosthesis against the native annulus. If the prosthesis is non-circumferentially centered relative to the native annulus, the deployed device can leak and dislodge from the native valve implantation site.

Embodiments hereof are directed to a circumferential and/or longitudinal centering device for use with a valve delivery system for a transcatheter valve prosthesis. A circumferential centering device according to embodiments hereof is configured to circumferentially center both the delivery system and the valve prosthesis in a vessel at the target implantation site, such as for example an aorta A and/or a native aortic valve AV. As used herein, "circumferentially centered" and/or "circumferentially center" include a device having a distal portion thereof that is placed or situated in the center of a body lumen such that a centerpoint of the distal portion of the device is equidistant to the vessel wall of the body lumen within a tolerance of 10% of the mean lumen diameter of the body lumen. As used herein, "lumen diameter" for a circular body lumen is the diameter of the circular lumen, "lumen diameter" for an eccentric or non-circular body lumen is the diameter of a circular lumen with an equivalent perimeter length, and "lumen diameter" for an oval body lumen is the average of the major and minor diameters of the oval lumen. The circumferential centering devices described herein prevent the valve delivery system from abutting against or hugging the vessel wall around curvatures thereof as described above with respect to FIG. 1. As such, the circumferential centering devices described herein allow a valve delivery system to self-center without the requirement that the user steer the valve delivery system to the center of the body lumen. In addition, the circumferential centering devices described herein may be utilized at any time during the delivery process. For example, although described herein primarily with respect to circumferentially centering the delivery system and valve prosthesis after the distal portion of the delivery system is positioned at the target native valve site but prior to deployment of the valve prosthesis, the circumferential centering devices described herein may be utilized before the distal portion of the delivery system is positioned at the target native valve site to circumferentially center the valve delivery system within a vessel while the delivery system is being tracked to the target native valve site.

A longitudinal centering device according to embodiments hereof is configured to longitudinally center the valve prosthesis at the target implantation site, such as for example a native aortic valve AV. As used herein, "longitudinally centered" and/or "longitudinally center" include a valve prosthesis having a distal end that is positioned or implanted between 2-4 mm distal to the native valve annulus within a tolerance of 10%. The longitudinal centering devices described herein prevent the valve prosthesis from being implanted too deep or too shallow into the left ventricle LV relative to the native annulus.

Figures 2, 2A:
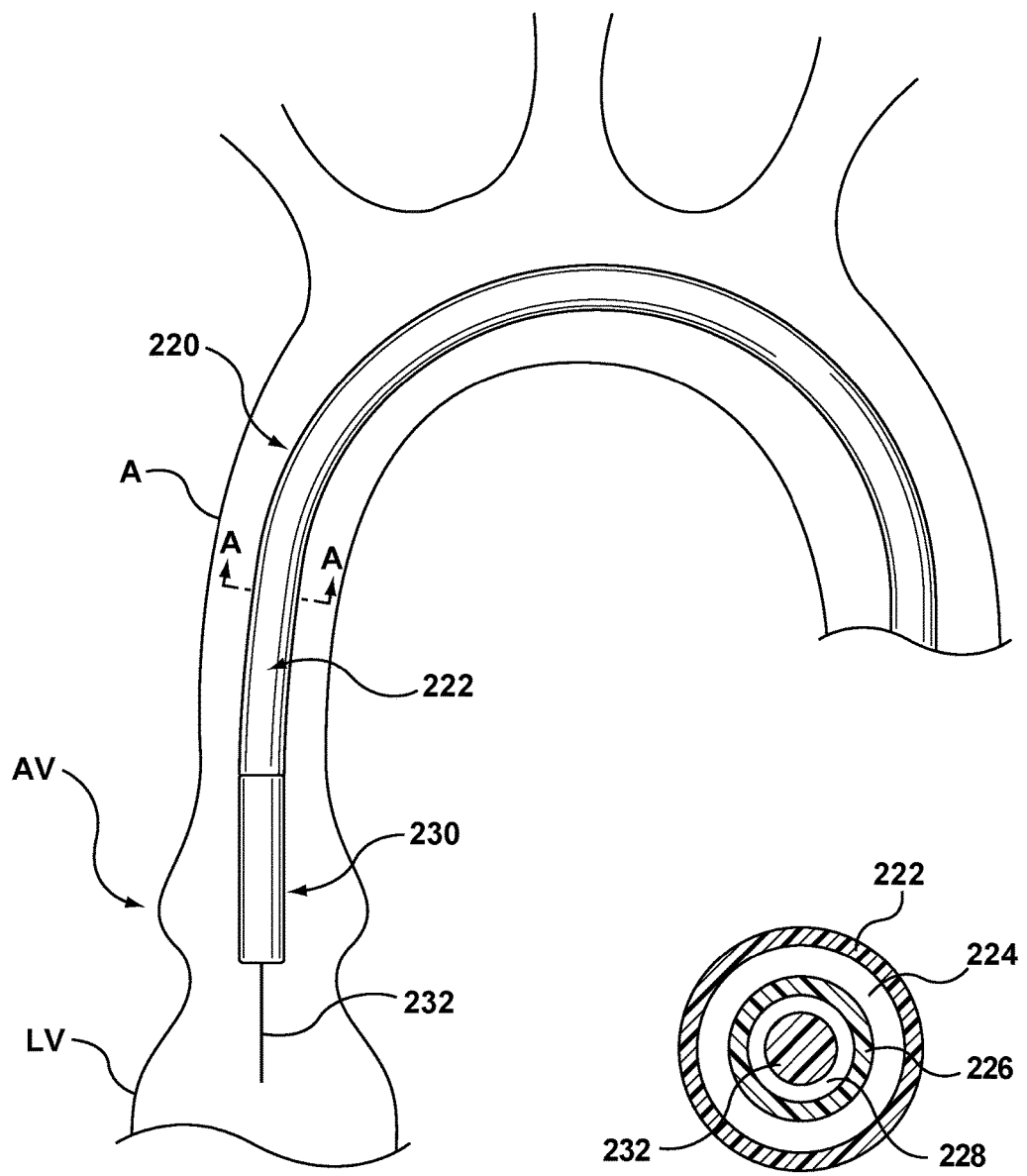
FIG. 2 is an illustration of a valve centering catheter having a circumferential centering device in situ according to an embodiment hereof, wherein the circumferential centering device is in a delivery or unexpanded configuration.
FIG. 2A is a cross-sectional view taken along line A-A of FIG. 2.

With reference to FIG. 2 and FIG. 2A, a valve centering catheter 220 is depicted in situ after being tracked over a guidewire 232, with a circumferential centering device 230 thereof in a delivery or unexpanded configuration. Circumferential centering device 230 is positioned at a distal end of valve centering catheter 220 in order to deploy within the annulus of the native aortic valve AV. In the embodiment of FIG. 2, circumferential centering device 230 is an inflatable balloon. Valve centering catheter 220 includes an outer shaft 222 and an inner shaft 226 defining a guidewire lumen 228 there-through. Guidewire lumen 228 of inner shaft 226 is sized to slidingly receive guidewire 232 such that valve centering catheter 220 is configured to be tracked over the guidewire during delivery thereof as shown in FIG. 2. In the coaxial catheter construction of the illustrated embodiment, inner shaft 226 extends within outer shaft 222 such that an annular inflation lumen 224 is defined between an inner surface of outer shaft 222 and an outer surface of inner shaft 226 to allow inflation fluid received through a hub (not shown) at a proximal end of valve centering catheter 220 to be delivered to balloon 122. As would be understood by one of ordinary skill in the art of balloon catheter design, the proximal end (not shown) of valve centering catheter 220 extends outside of a patient and includes a luer hub (not shown) or other type of fitting that may be connected to a source of inflation fluid. Other types of catheter construction are also amendable to the invention, such as, without limitation thereto, a catheter shaft formed by multi-lumen profile extrusion. In the embodiment of FIG. 2, valve centering catheter 220 has an over-the-wire (OTW) catheter configuration with inner shaft 226 defining guidewire lumen 228 that extends substantially the entire length of the catheter for accommodating a guidewire. In another embodiment (not shown), valve centering catheter 220 is modified to be of a rapid exchange (RX) catheter configuration without departing from the scope of the present invention such that inner shaft 226 extends within only the distal portion of valve centering catheter 220 incorporating a distal portion of inflation lumen 224.

Outer and inner shafts 222, 226 are formed of any suitable flexible polymeric material. Non-exhaustive examples of material for the shaft components are polyethylene terephalate (PET), nylon, polyethylene, PEBAX, or combinations of any of these, either blended or co-extruded. Optionally, a portion of the shaft components is formed as a composite having a reinforcement material incorporated within a polymeric body to enhance strength, flexibility, and/or toughness. Suitable reinforcement layers include braiding, wire mesh layers, embedded axial wires, embedded helical or circumferential wires, and the like. In an embodiment, the proximal portion of outer shaft 222 may in some instances be formed from a metallic tubing, such as a hypotube, or a reinforced polymeric tube as shown and described, for example, in U.S. Pat. No. 5,827,242 to Follmer et al., which is incorporated by reference herein in its entirety. The shaft components may have any suitable working length, for example, 550 mm-600 mm, to extend to a target location within the body vessel.

FIGS. 3, 3A, and 3B depict circumferential centering device 230 in a radially expanded or inflated configuration. FIG. 3 illustrates valve centering catheter 220 and circumferential centering device 230 in situ, while FIGS. 3A and 3B illustrate circumferential centering device 230 removed from valve centering catheter 220 for illustrative purposes only. FIG. 3A is an end view of circumferential centering device 230 while FIG. 3B is a perspective view. In the expanded or inflated configuration, circumferential centering device 230 is an annular component having a donut-shaped or tire-shaped configuration such that the cross-section thereof defines a central opening or lumen 238 there-through. U.S. Pat. No. 4,909,252 to Goldberger, incorporated by reference herein in its entirety, describes an annular or ring-shaped balloon that may be modified for use in embodiments hereof. In addition to providing perfusion and allowing blood flow there-through during the procedure, central opening or lumen 238 is sized and configured to allow a valve delivery system to be subsequently delivered through expanded circumferential centering device 230 in order to guide and circumferentially center the valve delivery system within the native valve annulus prior to deployment of the valve prosthesis contained within the valve delivery system. Stated another way, expanded circumferential centering device 230 is a docking or locating ring that is positioned within the native valve annulus at the beginning of a valve replacement/repair procedure in order to circumferentially center a later-introduced valve delivery system within the vessel for a more successful prosthetic valve deployment.

Expanded circumferential centering device 230 is an annular balloon having an outer wall or circumferential surface 234 and an inner wall or circumferential surface 236 with an interior space or volume 235 being defined between outer and inner walls 234, 236. Depending upon the size of the patient, outer wall 234 may diametrically vary from 30-50 mm and inner wall 236 can diametrically vary from 20-40 mm. Inner wall 236 is sized to be slightly greater than the outer profile of the valve delivery system in order to provide clearance there-between. At least a portion of circumferential centering device 230 is sealingly attached to outer shaft 222, and outer shaft 222 includes one or more ports (not shown) provide fluid communication between inflation lumen 224 and interior volume 235 of circumferential centering device 230. More particularly, as shown in FIG. 3C, circumferential centering device 230 is sealingly attached to a distal end of outer shaft 222 so as to be longitudinally offset with outer shaft 222. In another embodiment shown in FIG. 3D, a circumferential centering device 230D defining a central opening or lumen 238D there-through is sealingly attached to a distal end of an outer shaft 222D so as to be longitudinally aligned with outer shaft 222D. In another embodiment shown in FIG. 3E, a circumferential centering device 230E is sealingly attached to a distal end of an outer shaft 222E and coils or follows a circular path from outer shaft 222E in order to define a central opening or lumen 238E. When inflation fluid is provided within inflation lumen 224, it fills interior volume 235 of circumferential centering device 230 in order to inflate the circumferential centering device into the expanded configuration. In an embodiment hereof, the inflation fluid to inflate circumferential centering device 230 includes a contrast agent so that expanded circumferential centering device 230 provides constant visualization thereof during the valve replacement/repair procedure.

In another embodiment hereof, the circumferential centering device is an expandable braid or mesh component. More particularly, FIGS. 4 and 5 illustrate a circumferential centering device 430 in its expanded configuration. FIGS. 4 and 5 illustrate circumferential centering device 430 removed from a valve centering catheter for illustrative purposes only. FIG. 4 is an end view of circumferential centering device 430 while FIG. 4B is a perspective view. Circumferential centering device 430 includes a braided structure constructed from a plurality of metallic wires or filaments woven together or a stamped mesh 437 that has a tire-shaped or donut-shaped configuration such that a cross-section thereof defines a central opening or lumen 438 there-through to allow for subsequent delivery of a valve delivery system. Mesh 437 has an outer wall or circumferential surface 434 and an inner wall or circumferential surface 436, with an interior space or volume being defined there-between. Open spaces 439 defined by mesh 437 when circumferential centering device 430 is expanded allow blood or other fluid to flow there-through during the valve replacement/repair procedure such that the blood flow is not blocked or occluded. In an embodiment shown in FIG. 4, circumferential centering device 430 is self-expanding meaning it has a mechanical memory to return to the expanded or deployed configuration. Mechanical memory may be imparted to the braided wire or mesh structure that forms circumferential centering device 430 by thermal treatment to achieve a spring temper in stainless steel, for example, or to set a shape memory in a susceptible metal alloy, such as nitinol. Expandable circumferential centering device 430 is held or compressed in its delivery configuration within a sheath (not shown) so that circumferential centering device 430 is configured to be tracked through the vasculature in a low profile. When it is desired to expand circumferential centering device 430 into the annular tire-shaped or donut-shaped configuration, the sheath is withdrawn such that circumferential centering device 430 is released and allowed to assume its expanded configuration.

In another embodiment hereof, the circumferential centering device may include one or more anatomical markers to assist in alignment of the valve prosthesis during delivery thereof. More particularly, FIG. 6 illustrates a circumferential centering device 630 in its expanded configuration. FIG. 6 is an end view of circumferential centering device 630 and illustrates circumferential centering device 630 removed from a valve centering catheter for illustrative purposes only. Circumferential centering device 630 is an inflatable balloon with a central opening or lumen 638 there-through to allow for subsequent delivery of a valve delivery system. Prior to being inflated in situ, central opening 638 of circumferential centering device 630 has a circular cross-section similar to central opening 238 of circumferential centering device 230. However, circumferential centering device 630 is formed with a plurality of deformable regions 631A, 631B, 631C (collectively referred to herein as deformable regions 631) that are configured to conform to the surrounding or adjacent tissue of the native valve leaflets. When inflated in situ, deformable regions 230 are configured to project into or align with the three commissural points of the native valve leaflets of a native aortic valve, thereby resulting in a generally triangular cross-section of circumferential centering device 630 as shown in FIG. 6. When circumferential centering device 630 has a generally triangular cross-section, deformable regions 631 form three vertices of a triangle and three segments 633 extend between deformable regions 631. In an embodiment, deformable regions 631 are formed with a first material that is more flexible, compliant, or deformable than a second material of segments 633 extending there-between so that deformable regions 631 conform to or mate with the shape of the surrounding anatomy. In another embodiment hereof, deformable regions 631 and segments 633 extending there-between are formed from the same material but deformable regions 631 are relatively thinner than segments 633 so that the thin-walled deformable regions 631 conform to or mate with the shape of the surrounding anatomy. In yet another embodiment, deformable regions 631 and segments 633 extending there-between are formed from the same material and deformable regions 631 are heat-set in a deformed profile so that deformable regions 631 conform to or mate with the shape of the surrounding anatomy. When positioning a valve delivery system through lumen 638 of expanded circumferential centering device 630, deformable regions 631 serve or function as anatomical markers since the triangle vertices correspond to the three commissural points of the native valve leaflets. As such, deformable regions 631 assist in positioning the valve delivery system with the correct rotational alignment within the native valve.

Figure 7:
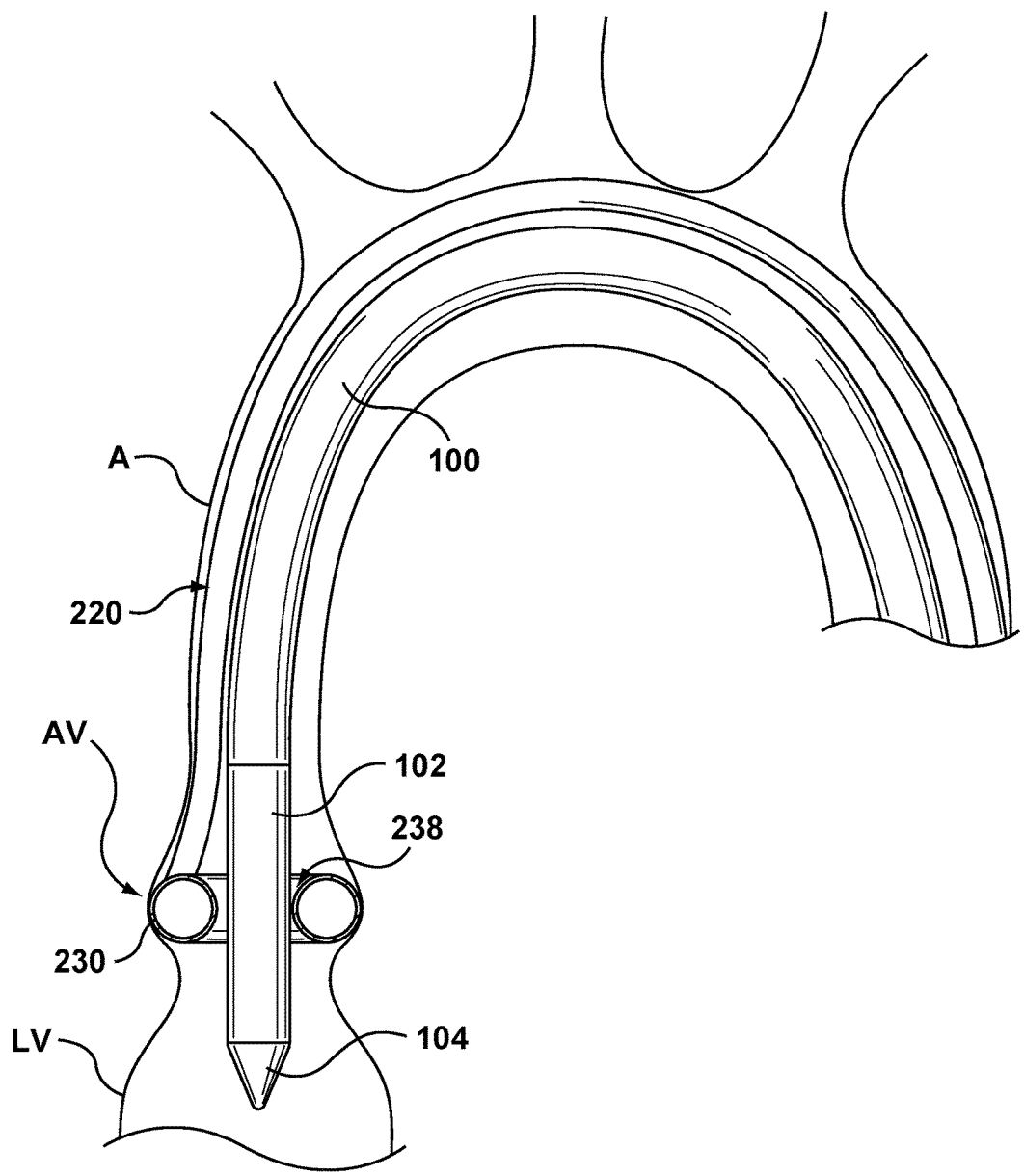
FIG. 7 is an illustration of a valve delivery system being positioned through the valve centering catheter of FIG. 2 in situ, wherein the circumferential centering device of the valve centering catheter is in a deployed or expanded configuration and a valve prosthesis of the valve delivery system is in a delivery or unexpanded configuration.

Turning back to FIG. 3, valve centering catheter 220 is illustrated in situ with circumferential centering device 230 in an inflated or expanded configuration. Once circumferential centering device 230 is positioned and expanded within the native valve annulus, valve delivery system 100 having a valve prosthesis 116 mounted thereon is delivered to the treatment site and advanced through central opening 238 of expanded circumferential centering device 230 as shown on FIG. 7. In FIG. 7, valve delivery system 100 is depicted with valve prosthesis 116 (obstructed in FIG. 7 but shown in FIG. 8) in a delivery or compressed configuration in which the valve prosthesis is loaded within distal capsule section 102 of the valve delivery system. Distal tip 104 of valve delivery system 100 is advanced beyond the native valve annulus and located within the left ventricle LV. Since valve delivery system 100 is delivered through central opening 238 of expanded circumferential centering device 230, valve delivery system 100 and the valve prosthesis mounted thereon are circumferentially centered within the native valve annulus of the native aortic valve AV.

Figure 8:
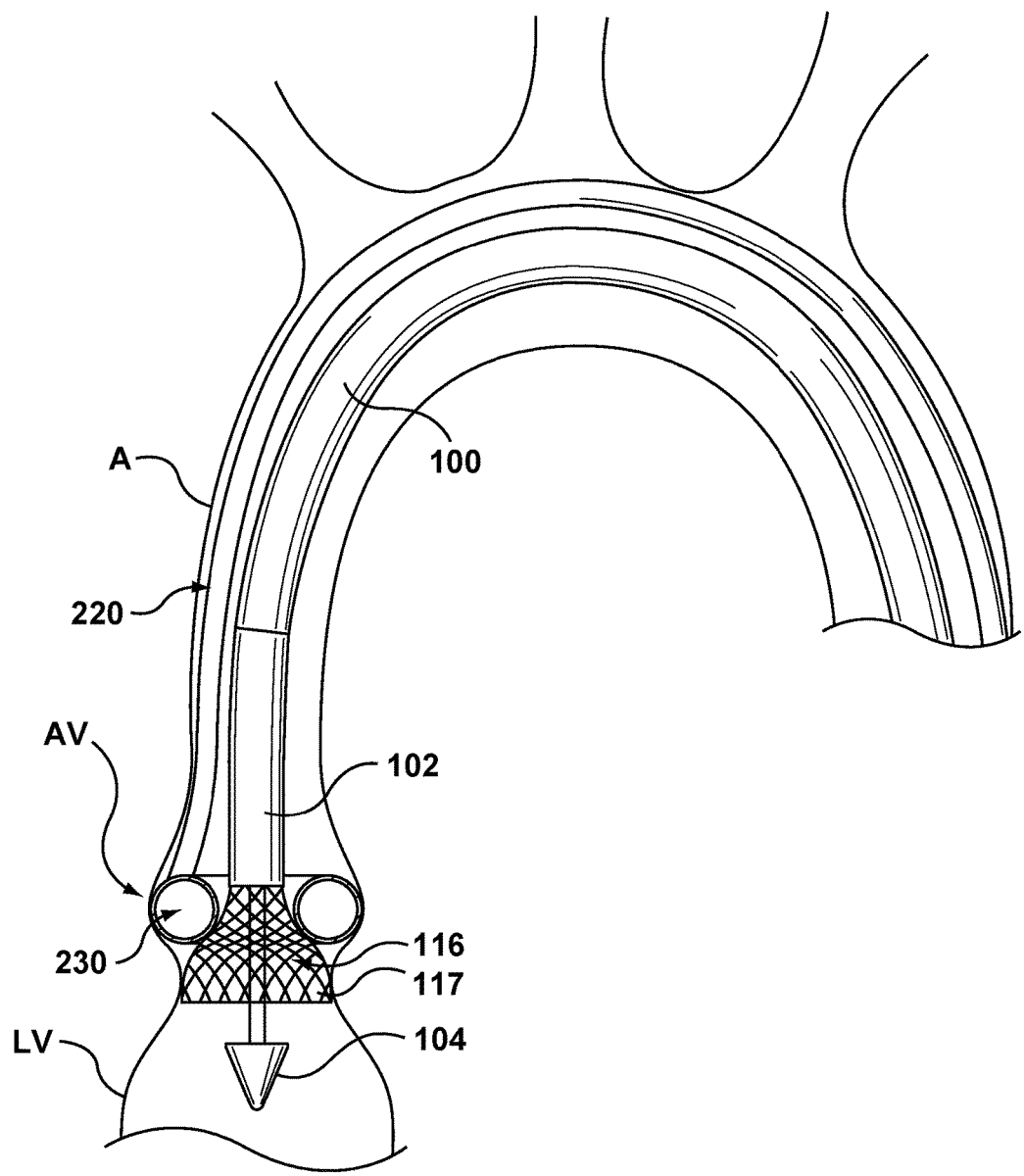
FIG. 8 is an illustration of the valve prosthesis of FIG. 7 being partially deployed in situ, wherein the circumferential centering device of the valve centering catheter is in a deployed or expanded configuration and a valve prosthesis of the valve delivery system is in a partially deployed configuration with only an inflow end thereof being expanded.

With valve centering catheter 220 and expanded circumferential centering device 230 still in place, valve prosthesis 116 is partially deployed as shown in FIG. 8. More particularly, distal capsule section 102 of valve delivery system 100 is proximally retracted to expose and release only an inflow end 117 of valve prosthesis 116. Inflow end 117 self-expands into apposition with the surrounding native anatomy of the native aortic valve AV, thereby anchoring valve prosthesis 116 and securing the circumferentially centered position of valve prosthesis 116 relative to the native valve annulus of the native aortic valve AV. Distal capsule section 102 remains disposed over at least an outflow end 115 (obstructed in FIG. 8 but shown in FIG. 10) of valve prosthesis 116.

Figure 9:
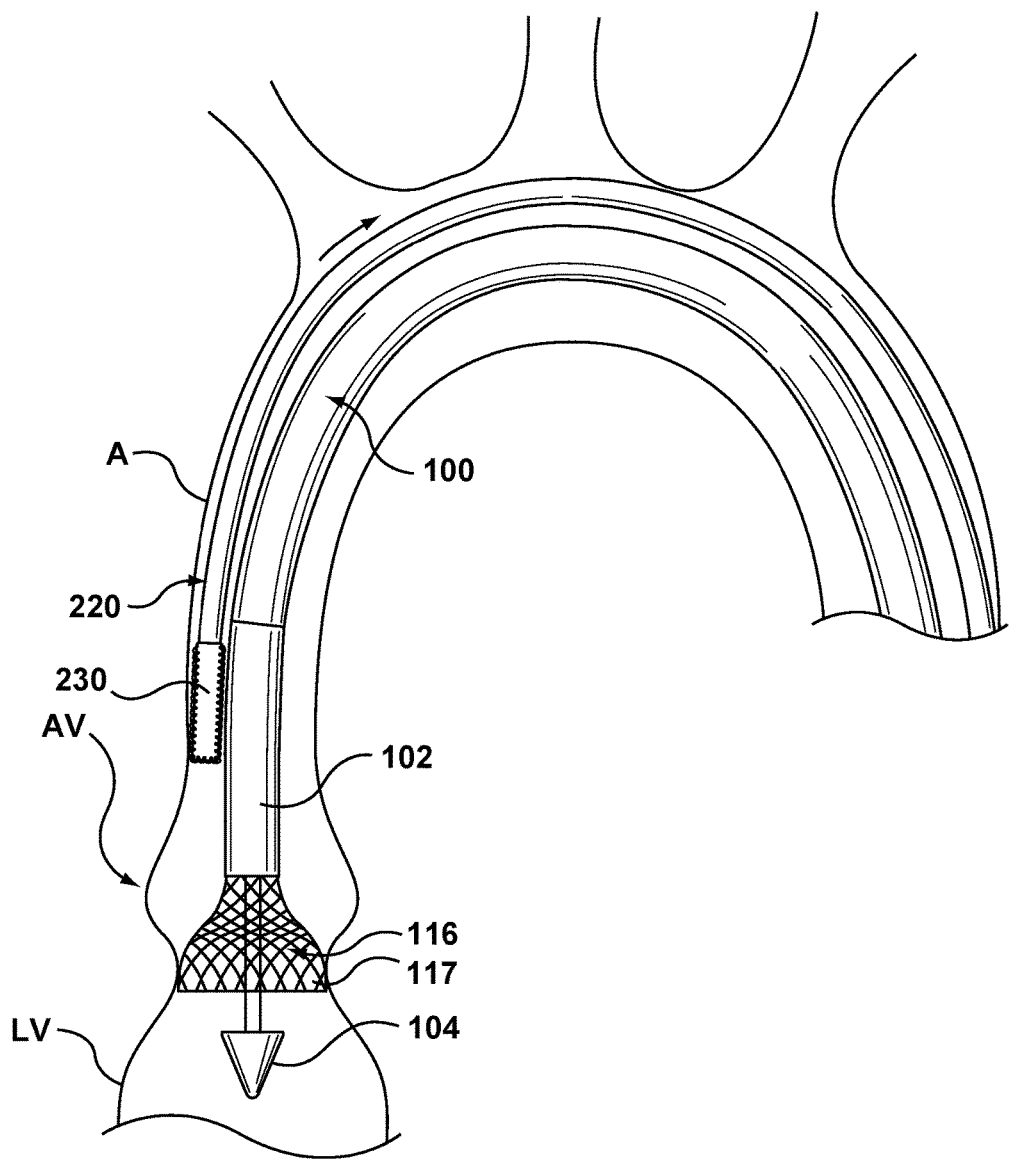
FIG. 9 is an illustration of the valve centering catheter of FIG. 8 during removal thereof after partial deployment of the valve prosthesis, wherein the circumferential centering device of the valve centering catheter is in a delivery or unexpanded configuration and a valve prosthesis of the valve delivery system is in a partially deployed configuration with only an inflow end thereof being expanded.

After partial deployment of valve prosthesis 116 is achieved as desired, circumferential centering device 230 is deflated or unexpanded and valve centering catheter 220 is removed as shown in FIG. 9. Since outflow end 115 (obstructed in FIG. 9 but shown in FIG. 10) of valve prosthesis 116 is still contained or compressed within distal capsule section 102 of valve delivery system 100, deflated circumferential centering device 230 is retracted and passes by the compressed outflow end of the valve prosthesis without any interference. During removal of valve centering catheter 220, deployed inflow end 117 of valve prosthesis 116 ensures that the valve prosthesis remains circumferentially centered within the native valve annulus and also ensures that valve prosthesis 116 is not inadvertently dislodged during removal of valve centering catheter 220.

Figure 10:
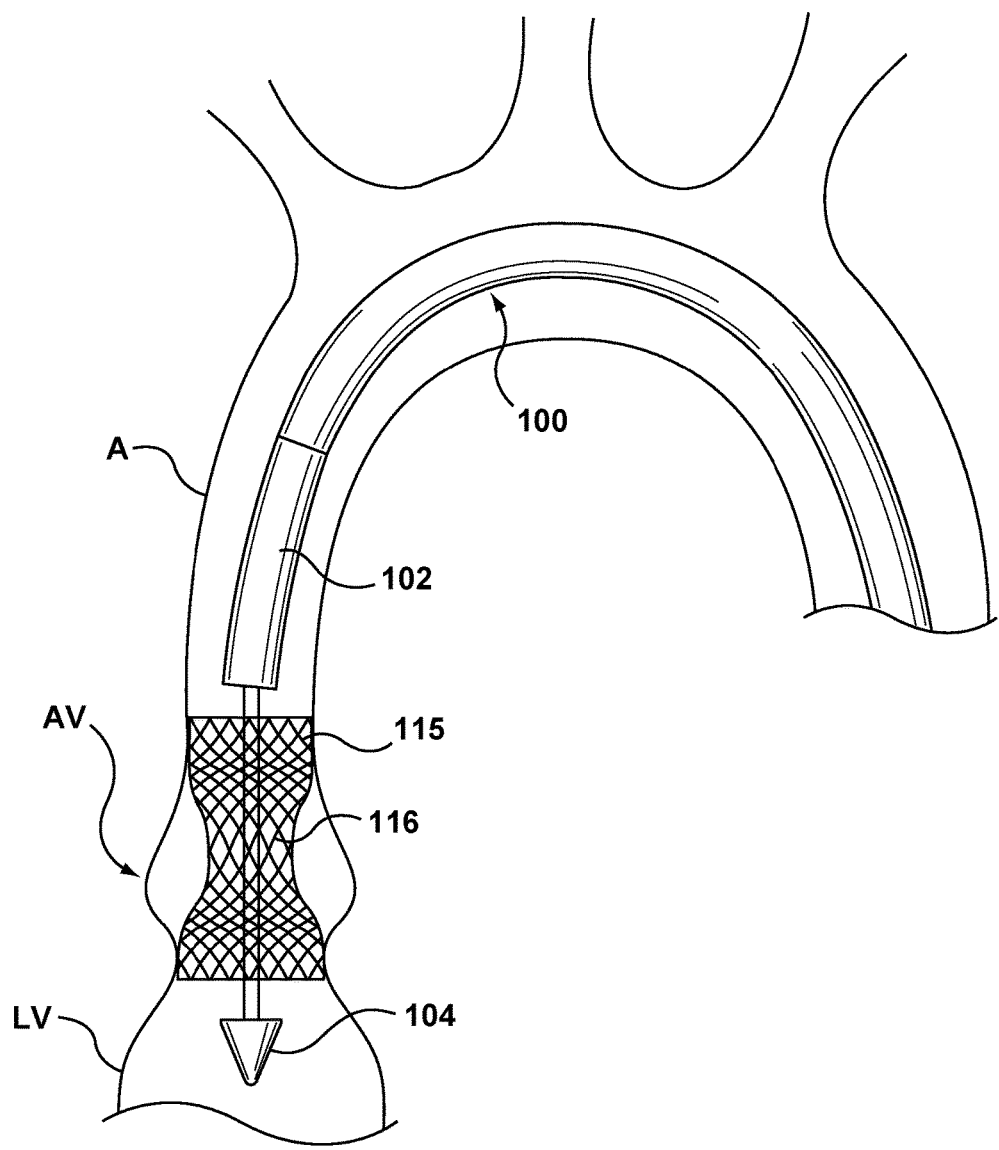
FIG. 10 is an illustration of the valve prosthesis of FIG. 9 being fully deployed in situ after removal of the valve centering catheter.

After valve centering catheter 220 is removed, valve prosthesis 116 is fully deployed or expanded as shown in FIG. 10. More particularly, distal capsule section 102 of valve delivery system 100 is proximally retracted to expose and release the entire length of valve prosthesis 116. Outflow end 115 of valve prosthesis 116 self-expands into apposition with the surrounding native anatomy.

Figure 11:
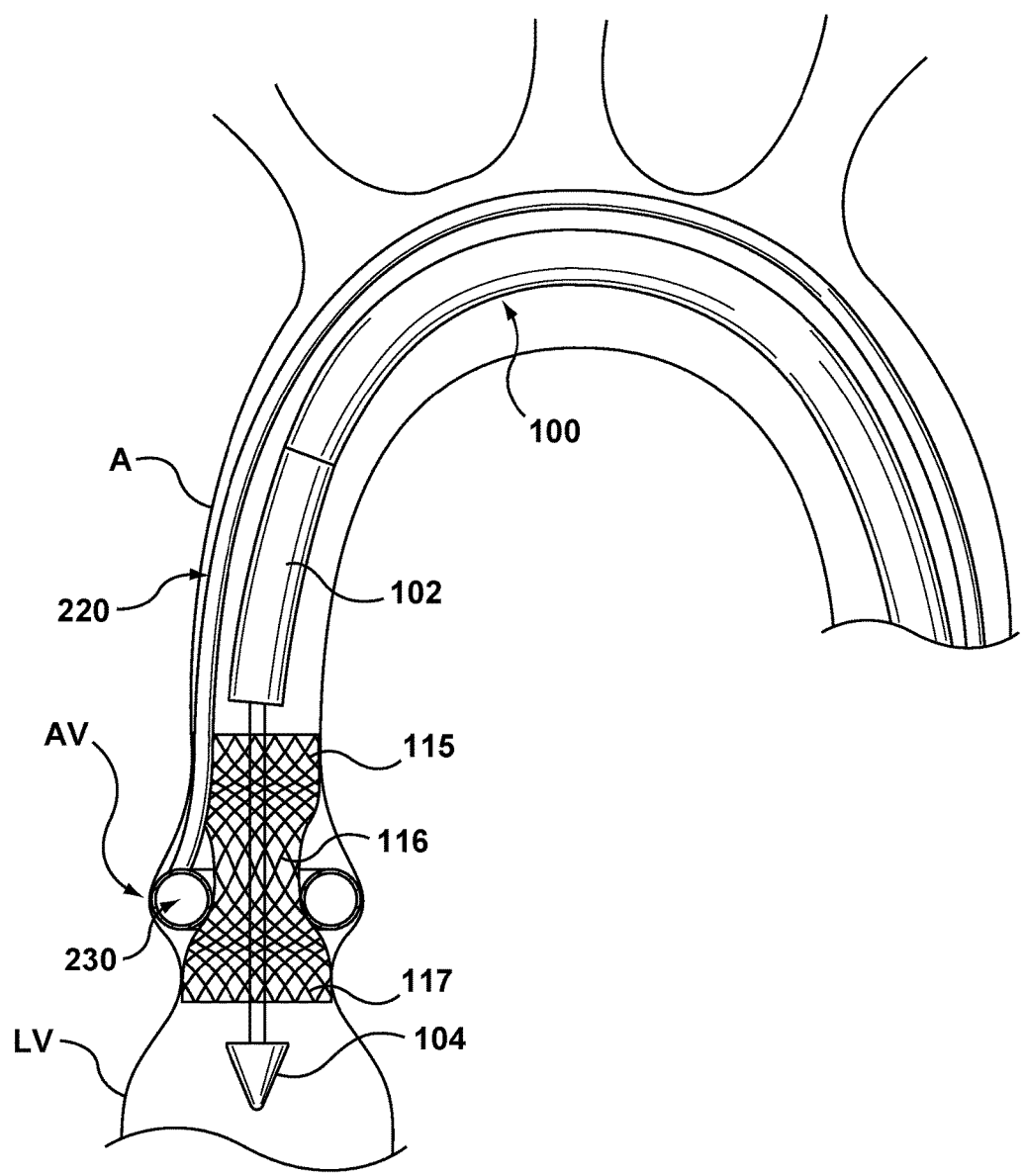
FIG. 11 is an illustration of the valve prosthesis of FIG. 8 being fully deployed in situ without removal of the valve centering catheter according to another embodiment hereof, wherein the circumferential centering device of the valve centering catheter is in a deployed or expanded configuration and a valve prosthesis of the valve delivery system is in a fully deployed configuration with both the inflow and outflow ends thereof being expanded.

In another embodiment hereof, the valve prosthesis is fully deployed prior to deflating and removing the circumferential centering device. More particularly, with reference to FIG. 11, with valve centering catheter 220 and expanded circumferential centering device 230 still in place, valve prosthesis 116 is fully deployed as shown in FIG. 11 such that both inflow end 117 and outflow end 115 self-expand into apposition with the surrounding native anatomy. Circumferential centering device 230 is then deflated, and the deflated circumferential centering device is removed past the deployed outflow end 115 of the valve prosthesis. Valve centering catheter 220 and deflated circumferential centering device 230 are of a sufficiently small diameter or profile so that circumferential centering device 230 may slip by or past the deployed outflow end 115 in the deflated state without dislodging the valve prosthesis.

Figure 12:
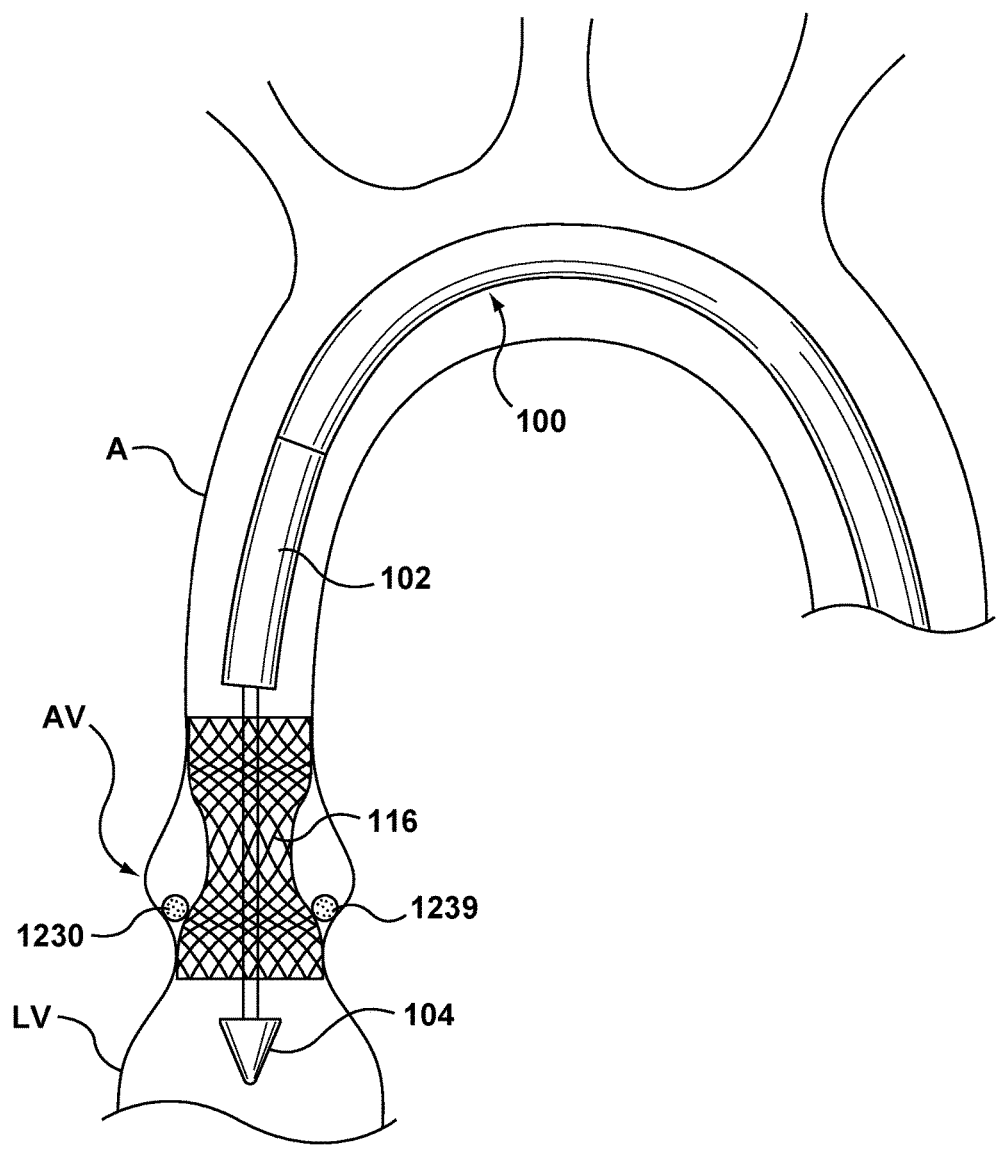
FIG. 12 is an illustration of a circumferential centering device according to another embodiment hereof, wherein the circumferential centering device is removable or detachable from a valve centering catheter and the circumferential centering device is shown in a deployed or expanded configuration and a valve prosthesis of the valve delivery system is shown in a fully deployed configuration with both the inflow and outflow ends thereof being expanded.

In another embodiment hereof, the circumferential centering device is configured to be removable or detachable from the valve centering catheter and is configured to remain in the expanded configuration in situ with the deployed valve prosthesis. More particularly, with reference to FIG. 12, circumferential centering device 1230 is similar to circumferential centering device 230 in that it includes an inflatable balloon that has a ring-shaped or donut-shaped configuration defining a central opening or lumen (not shown in FIG. 12) there-through to allow for subsequent delivery of valve delivery system 100. In this embodiment, however, circumferential centering device 1230 is expanded via a self-expanding injectable substance 1239. Suitable materials for self-expanding injectable substance 1239 include but are not limited to a liquid polymer, hydrogel or a collagen foam/sponge similar to the material commercially available under the trademark Angioseal. Self-expanding injectable substance 1230 solidifies or firms in a predetermined, such as but not limited to 60 seconds, after delivery into circumferential centering device 1230. In addition, in this embodiment, circumferential centering device 1230 is detachable from the valve centering catheter (not shown in FIG. 12) so that circumferential centering device 1230 be configured to remain in the expanded configuration in situ with the deployed valve prosthesis 116 as shown in FIG. 12. For example, circumferential centering device 1230 is detachable from the valve centering catheter via a threaded connection (not shown) there-between such that the valve centering catheter may be rotated or screwed to detach the circumferential centering device or via a weakened or breakable connection (not shown) there-between such that force may be applied to the valve centering catheter in order to break or snap the connection and detach the circumferential centering device. Other detachable mechanisms include but are not limited to an integral suture release mechanism (not shown) built into the valve centering catheter or an integral cutting or shearing tool (not shown) built into the valve centering catheter. In addition to circumferentially centering valve delivery system 100, circumferential centering device 1230 serves as a sealing element that remains in situ to provide a seal between an outer surface of valve prosthesis 116 and the surrounding native anatomy. Expanded circumferential centering device 1230 blocks retrograde blood flow around the outside of valve prosthesis 116, thereby minimizing and/or eliminating any paravalvular leakage at the implantation site. Since expanded circumferential centering device 1230 remains in situ, placement thereof may vary from other circumferential centering devices described herein because circumferential centering device 1230 must be positioned to avoid blocking the coronary arteries.

Figures 13, 14:
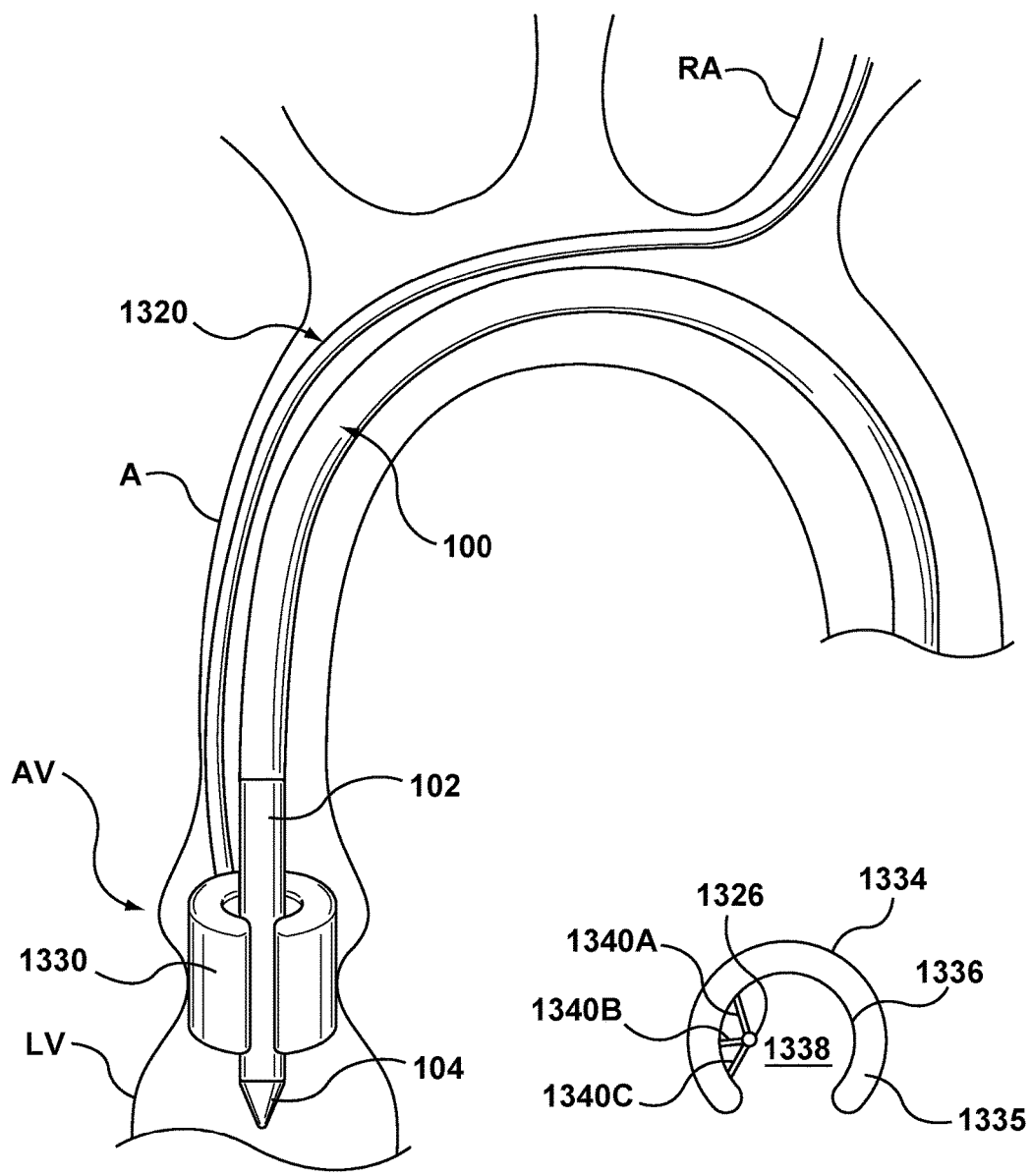
FIG. 13 is an illustration of a valve delivery system being positioned through a valve centering catheter in situ according to another embodiment hereof, wherein a circumferential centering device of the valve centering catheter has a C-shaped cross-section and is shown in a deployed or expanded configuration and a valve prosthesis of the valve delivery system is in a delivery or unexpanded configuration.
FIG. 14 is an end view of the valve centering catheter of FIG. 13, wherein the circumferential centering device is in a deployed or expanded configuration.

In another embodiment hereof, the circumferential centering device may have a C-shaped cross-section rather than an annular or ring-shaped cross-section. The C-shaped cross-section provides sufficient contact with native anatomy to ensure alignment of a subsequently delivered valve delivery system, but the C-shaped cross-section has smaller or reduced profile than an annular balloon. Advantageously, the reduced profile allows the circumferential centering device with a C-shaped cross-section to be delivered via the radial artery (labeled as RA in FIG. 13) and thus delivery of the circumferential centering device does not interfere with devices being delivered via the femoral artery, which may include valve delivery system 100 and a contrast delivery system (not shown). More particularly, with reference to FIGS. 13 and 14, circumferential centering device 1330 is an inflatable balloon that has a C-shaped cross-section defining a central opening or lumen 1338 there-through configured for subsequent delivery of valve delivery system 100. Circumferential centering device 1330 is shown in its expanded or inflated configuration in FIGS. 13 and 14. Circumferential centering device 1330 is an annular balloon having an outer wall or circumferential surface 1334 and an inner wall or circumferential surface 1336 with an interior space or volume 1335 being defined between outer and inner walls 1334, 1336. As best shown on FIG. 14, which illustrates an end view of valve centering catheter 1320, valve delivery system 1320 includes an inner or guidewire shaft 1326 and three eccentric inflation fingers 1340A, 1340B, 1340C (collectively referred to herein as inflation fingers 1340) for delivery of inflation fluid to the interior of circumferential centering device 1330. The eccentric inflation fingers 1340 ensure uniform expansion of circumferential centering device 1330, while minimizing interference with central opening or lumen 1338 which is required to be unobstructed in order to allow for subsequent delivery of valve delivery system 100. Inflation fingers 1340 are tubular components that are integral or formed as part of circumferential centering device 1330 in order to connect circumferential centering device 1330 to the inflation lumen (not shown) of valve centering catheter 1320.

In another embodiment hereof, a first or circumferential centering device is utilized to circumferentially center a valve prosthesis with a native aortic valve and a second or longitudinal centering device is utilized as a depth marker or reference point to longitudinally center a valve prosthesis by preventing the valve prosthesis from being positioned too deep or too shallow within the left ventricle. More particularly, with reference to FIG. 15, a valve centering catheter 1520 is percutaneously introduced into a vasculature. As shown on FIG. 15, valve centering catheter 1520 was previously tracked over a guidewire 1532 having an outer diameter of 0.030 inches or less to the native valve treatment site. Proximal to the centering component thereof that will be described in more detail below, valve centering catheter 1520 is constructed to have an outer diameter of 0.035 inches such that a valve delivery system may be subsequently delivered or tracked over the valve centering catheter as will be described in more detail herein. Valve centering catheter 1520 has a longitudinal centering device 1550 at a distal portion thereof, and valve centering catheter 1520 is illustrated in situ with longitudinal centering device 1550 in a delivery or unexpanded configuration. Longitudinal centering device 1550 is positioned at a distal end of valve centering catheter 1520 and is configured to deploy distal to or below the annulus of the native aortic valve AV as will be described in more detail herein.

Figure 15:
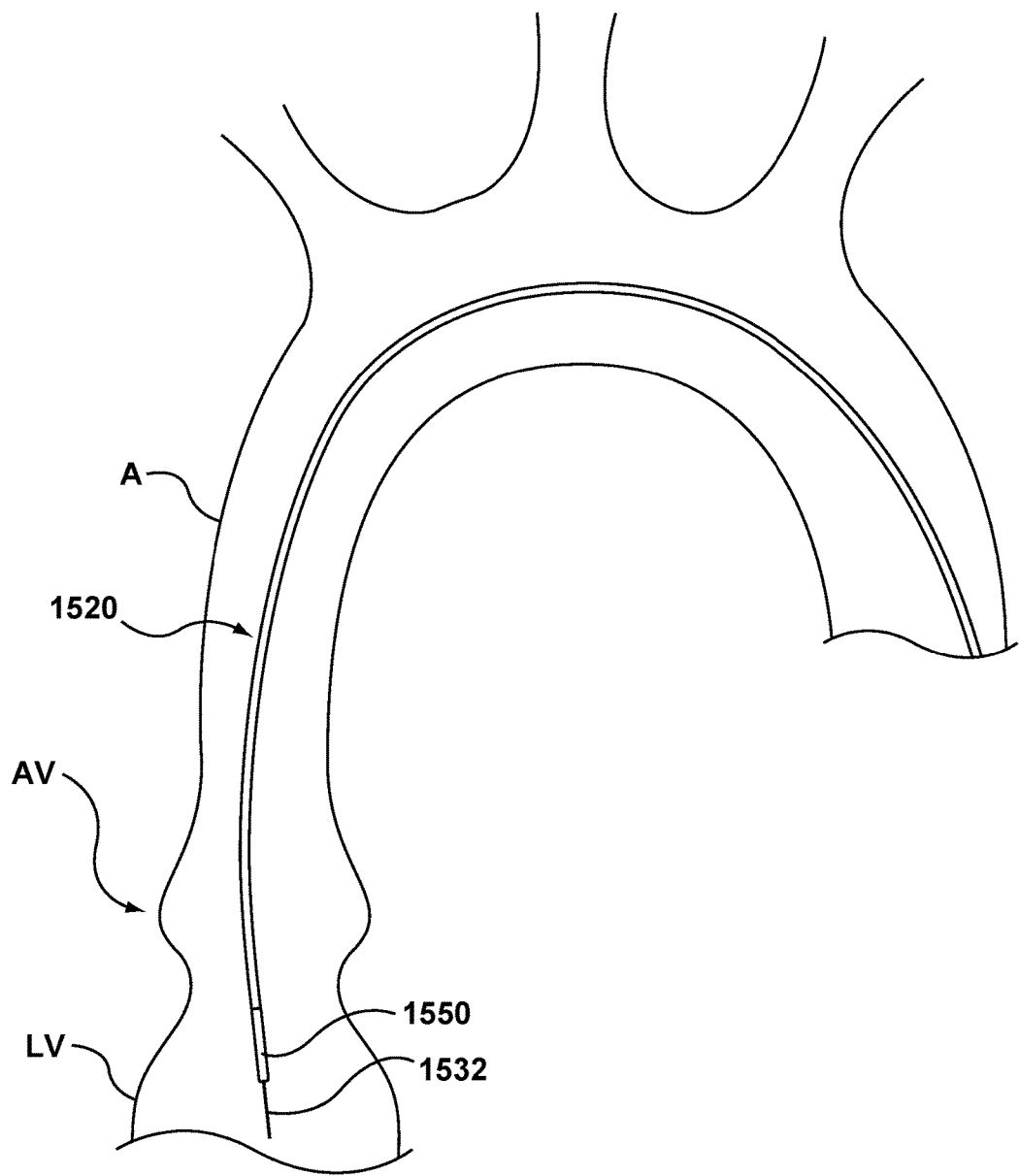
FIG. 15 is an illustration of a valve centering catheter having a longitudinal centering device in situ according to another embodiment hereof, wherein the longitudinal centering device is in a delivery or unexpanded configuration.
Figure 16:
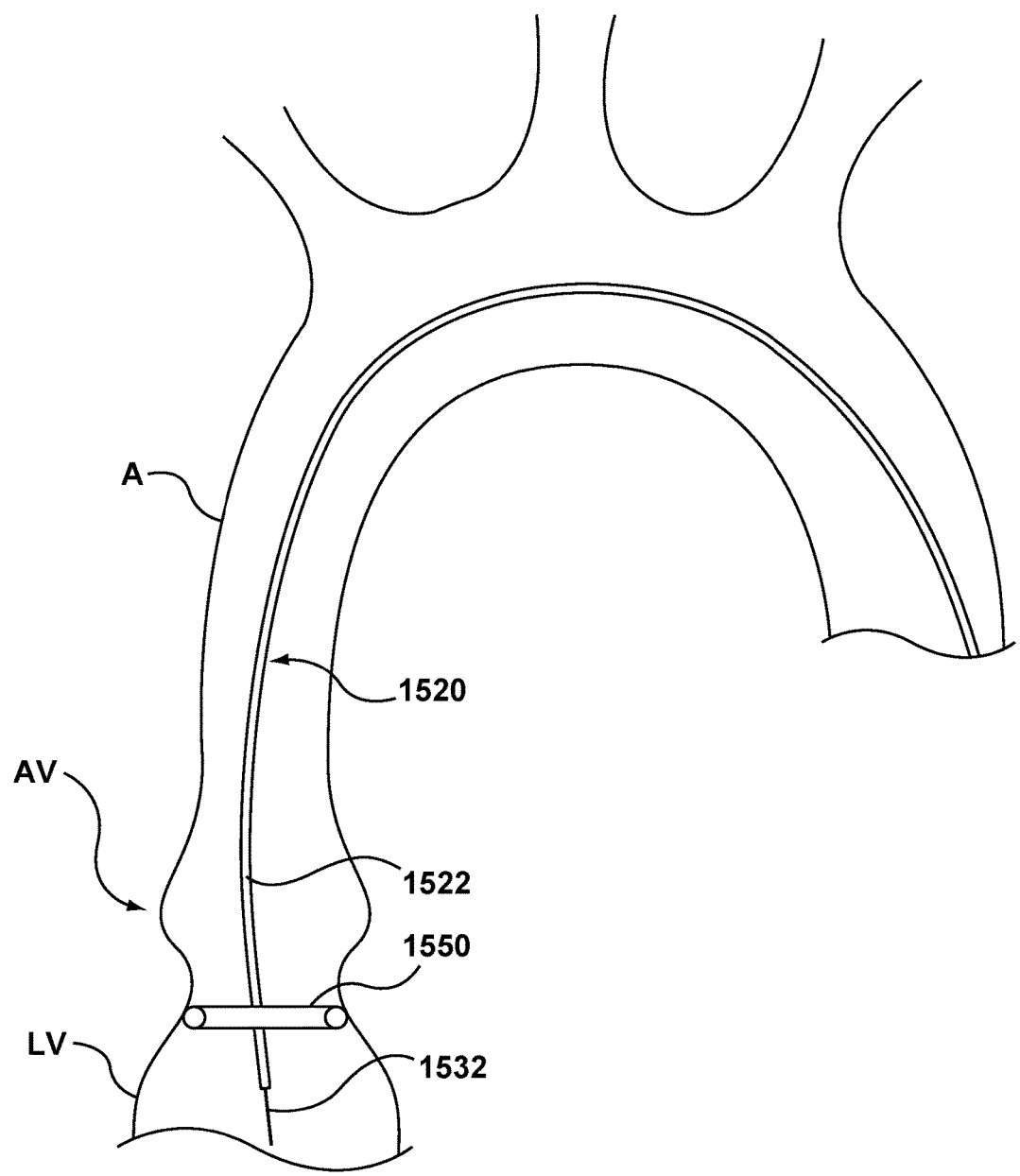
FIG. 16 is an illustration of the valve centering catheter of FIG. 15 in situ, wherein the longitudinal centering device is in a deployed or expanded configuration.
Figure 16A:
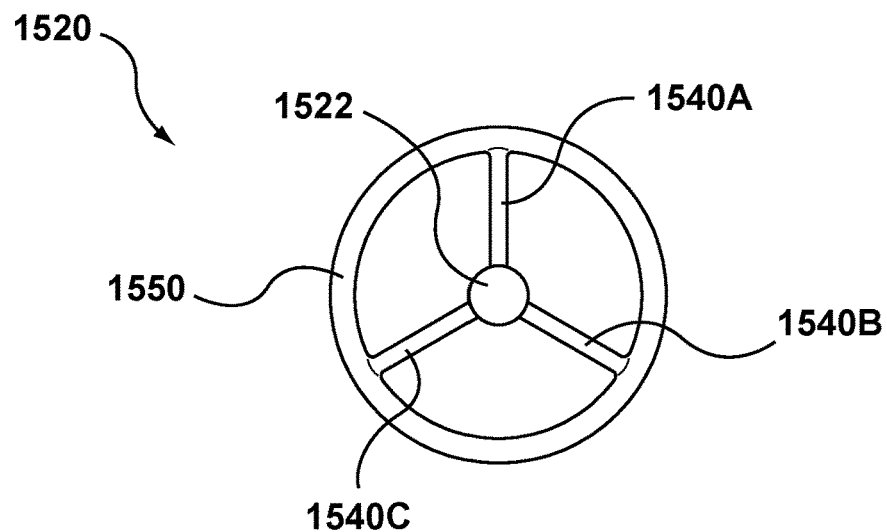
FIG. 16A is an end view of the valve centering catheter of FIG. 15, wherein the longitudinal centering device is in a deployed or expanded configuration.
Figure 16B:
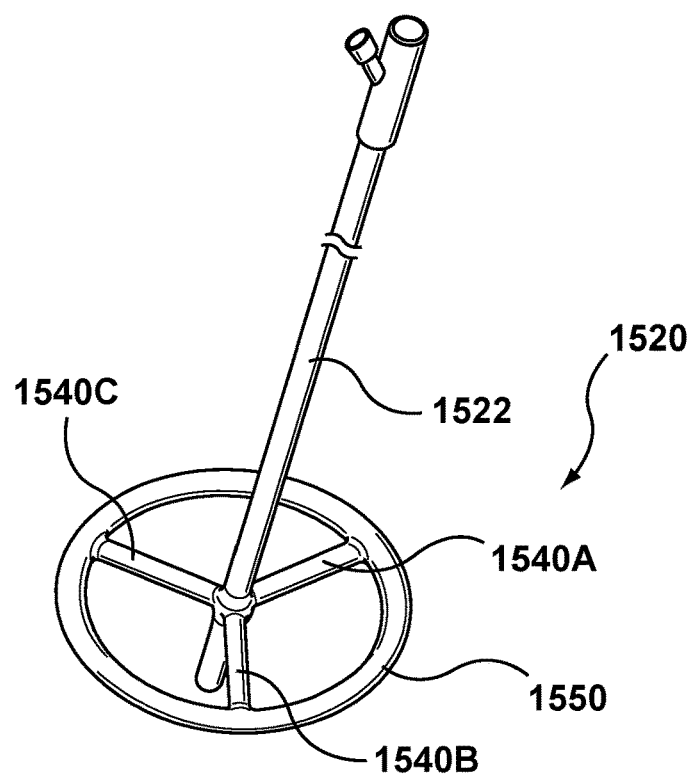
FIG. 16B is a perspective view of the valve centering catheter of FIG. 15, wherein the longitudinal centering device is in a deployed or expanded configuration.

In the embodiment of FIG. 15, longitudinal centering device 1550 is an annular inflatable balloon and valve centering catheter 1520 has a structure or configuration similar to valve centering catheter 220 described above. More particularly, similar to circumferential centering device 230, in the expanded or inflated configuration, longitudinal centering device 1550 has a tire-shaped or donut-shaped configuration defining a central opening or lumen (not shown in FIG. 15) there-through to allow for perfusion or blood flow during the valve replacement/repair procedure. At least a portion of longitudinal centering device 1550 is sealingly attached to an outer shaft 1522 of valve centering catheter 1520, and outer shaft 1522 includes one or more ports (not shown) provide fluid communication between an inflation lumen (not shown in FIG. 15) and an interior volume of longitudinal centering device 1550. More particularly, as best shown on FIGS. 16A and 16B, which illustrates an end view and a perspective view respectively of valve centering catheter 1520, valve delivery system 1520 includes three radially-extending inflation fingers 1540A, 1540B, 1540C (collectively referred to herein as radially-extending inflation fingers 1540) for delivery of inflation fluid to the interior of longitudinal centering device 1550. The radially-extending inflation fingers 1540 ensure uniform expansion of longitudinal centering device 1550 and also position or dispose outer shaft 1522 through the center of longitudinal centering device 1550. Radially-extending inflation fingers 1540 are tubular components that are integral or formed as part of longitudinal centering device 1550 in order to connect longitudinal centering device 1550 to the inflation lumen of valve centering catheter 1520. When inflation fluid is provided within the inflation lumen, it fills the interior volume of longitudinal centering device 1550 in order to inflate the longitudinal centering device into the expanded configuration. Expanded longitudinal centering device 1550 is a depth control marker or ring that is positioned below the native valve annulus at the beginning of a valve replacement/repair procedure in order to longitudinally center a later-introduced valve delivery system within the vessel for a more successful prosthetic valve deployment.

Valve centering catheter 1520 is tracked through the vasculature until longitudinal centering device 1550 is positioned distal to or beyond the native valve annulus and/or adjacent to the interior surfaces of the left ventricle. Once positioned as desired distal to or below the native valve annulus, longitudinal centering device 1550 is expanded or inflated to its annular configuration as shown on FIG. 16. In an embodiment hereof, the inflation fluid to inflate longitudinal centering device 1550 includes a contrast agent so that expanded longitudinal centering device 1550 provides constant visualization thereof during the valve replacement/repair procedure. In this embodiment, longitudinal centering device 1550 is positioned below the native valve annulus and/or adjacent to the interior surfaces of the left ventricle in order to serve as a marker or reference indicator for depth control during delivery of the valve delivery system and thereby longitudinally center the valve prosthesis of the valve delivery system.

Figure 17:
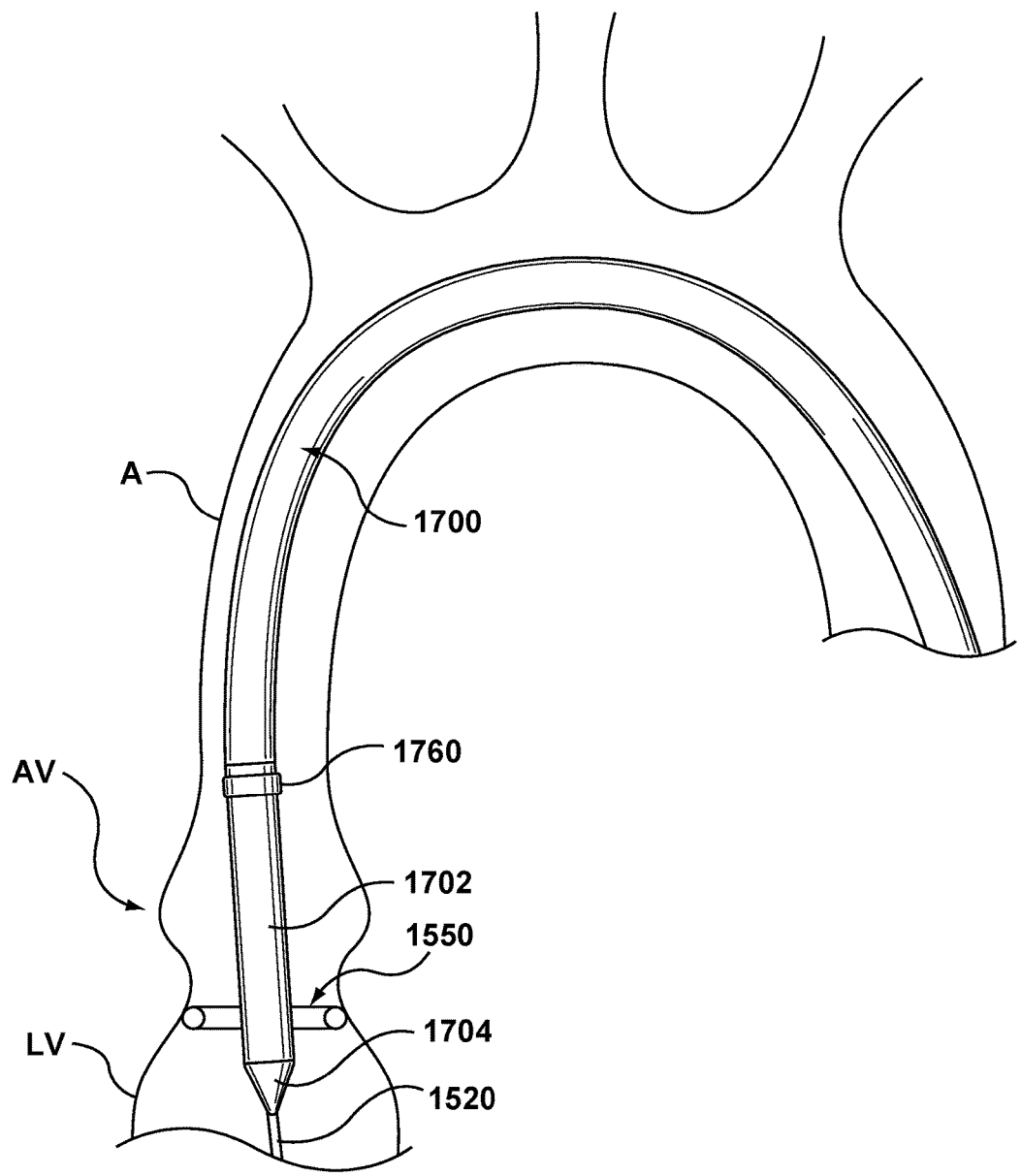
FIG. 17 is an illustration of a valve delivery system being positioned through the valve centering catheter of FIG. 16 in situ, wherein the longitudinal centering device of the valve centering catheter is in a deployed or expanded configuration, a circumferential centering device of the valve delivery system is in a delivery or unexpanded configuration, and a valve prosthesis of the valve delivery system is in a delivery or unexpanded configuration.

Once longitudinal centering device 1550 is radially expanded or inflated, a valve delivery system 1700 is percutaneously introduced into the vasculature and is advanced or tracked over valve centering catheter 1520 to the treatment site as shown in FIG. 17. In FIG. 17, valve delivery system 1700 is depicted with a valve prosthesis (not shown) in a delivery or compressed configuration in which the valve prosthesis is loaded within a distal capsule section 1702 of the delivery system. Distal tip 1704 of valve delivery system 1700 is advanced beyond the native valve annulus and through the central opening of the expanded longitudinal centering device 1550, which serves as a marker for depth control during delivery of valve delivery system 1700 to prevent distal tip 1704 from protruding too deep or too shallow into the left ventricle LV. Stated another way, valve delivery system 1700 is tracked through the vasculature until the valve prosthesis is positioned at the treatment site, proximal to expanded longitudinal centering device 1550, in order to longitudinally or axially center the valve prosthesis within the native valve annulus.

Valve delivery system 1700 includes a circumferential centering device 1760 proximal to the valve prosthesis. In the embodiment of FIG. 17, circumferential centering device 1760 is integrated onto distal capsule section 1702 of valve delivery system 1700 and is shown in a delivery or unexpanded configuration. Similar to circumferential centering device 230, circumferential centering device 1760 is an annular inflatable balloon that has a tire-shaped or donut-shaped configuration defining a central opening or lumen (not shown in FIG. 17) there-through to allow for perfusion or blood flow during the valve replacement/repair procedure. At least a portion of circumferential centering device 1760 is sealingly attached to distal capsule section 1702 of valve delivery system 1700, and distal capsule section 1702 includes one or more ports (not shown) provide fluid communication between an inflation lumen (not shown) and an interior volume of circumferential centering device 1760. In an embodiment, valve delivery system 1700 includes a plurality of radially-extending inflation fingers (not shown but similar to radially-extending inflation fingers 1540 described above with respect to FIGS. 16A and 16B) to ensure uniform expansion of circumferential centering device 1760 and also position or dispose distal capsule section 1702 through the center of circumferential centering device 1760.

Figure 18:
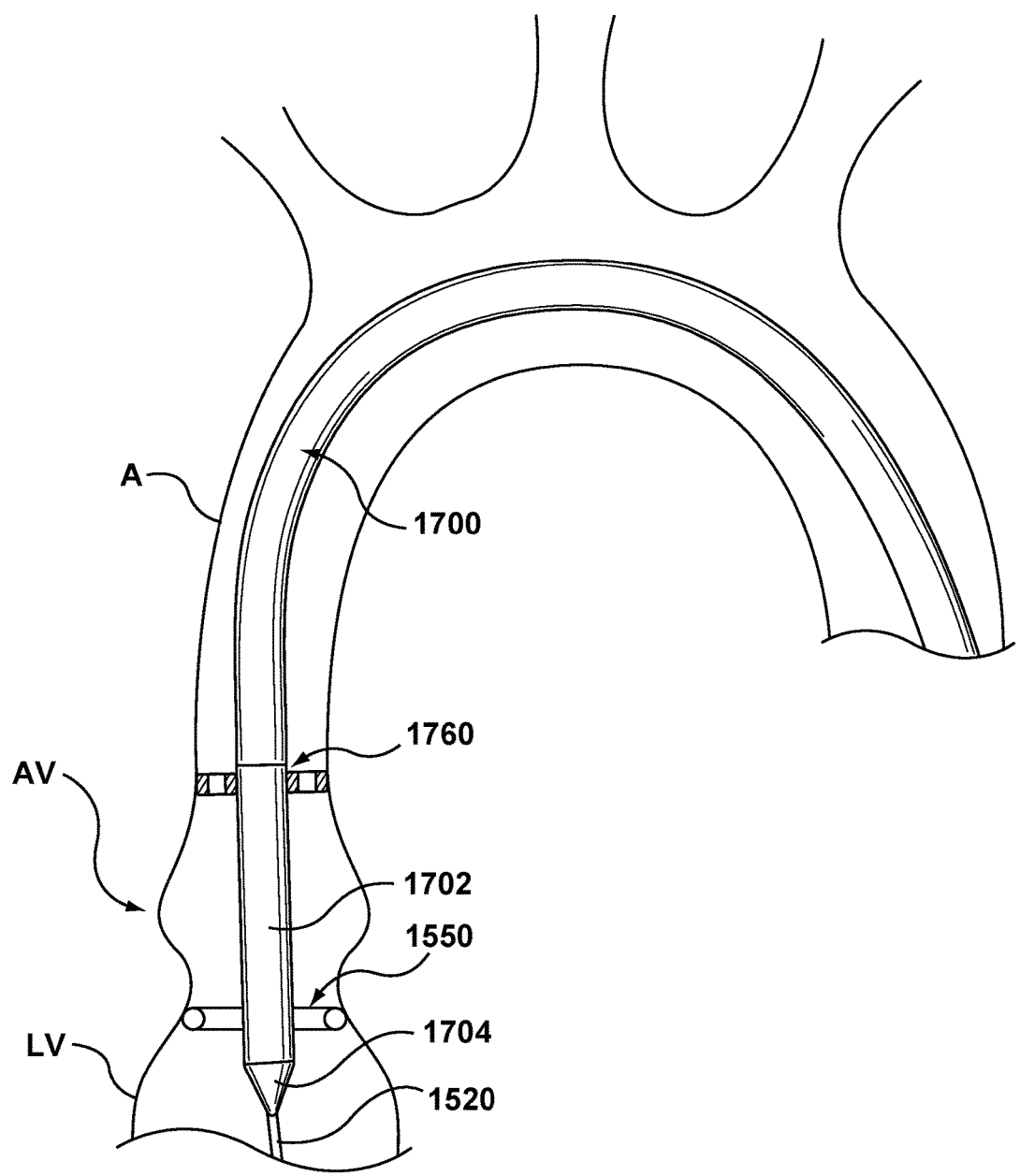
FIG. 18 is an illustration of the circumferential centering device of the valve delivery system of FIG. 17 being deployed in situ, wherein the longitudinal centering device of the valve centering catheter is in a deployed or expanded configuration, the circumferential centering device of the valve delivery system is in a deployed or expanded configuration, and a valve prosthesis of the valve delivery system is in a delivery or unexpanded configuration.

After valve delivery system 1700 is longitudinally positioned as described above, circumferential centering device 1760 of valve delivery system 1700 is radially expanded or inflated into an expanded configuration in order to circumferentially center valve delivery system 1700 and the valve prosthesis mounted thereon as shown in FIG. 18. In an embodiment hereof, the inflation fluid to inflate circumferential centering device 1760 includes a contrast agent so that expanded circumferential centering device 1760 provides constant visualization thereof during the valve replacement/repair procedure. Depending upon patient anatomy and the longitudinal location of circumferential centering device 1760 on distal capsule section 1702, circumferential centering device 1760 may be positioned to deploy within the native valve annulus, proximal to the native valve annulus, and/or within ascending aorta. The valve prosthesis is then deployed into apposition with the native anatomy, thereby anchoring and securing the longitudinally and circumferentially centered position of the valve prosthesis within the native valve. Accordingly, longitudinal centering device 1550 acts as a centering balloon distal to capsule and circumferential centering device 1760 is proximal to the capsule giving two points on centering to ensure that the valve delivery system is maintained coaxial to the annulus during deployment. In the embodiment of FIGS. 17 and 18 in which circumferential centering device 1760 is integrated onto distal capsule section 1702 of valve delivery system 1700, circumferential centering device 1760 is formed from an elastic material configured to stretch when distal capsule section 1702 is retracted during deployment of the valve prosthesis. As such, inflated circumferential centering device 1760 remains expanded and in contact with the surrounding native anatomy during retraction of distal capsule section 1702 and deployment of the valve prosthesis.

Figure 19:
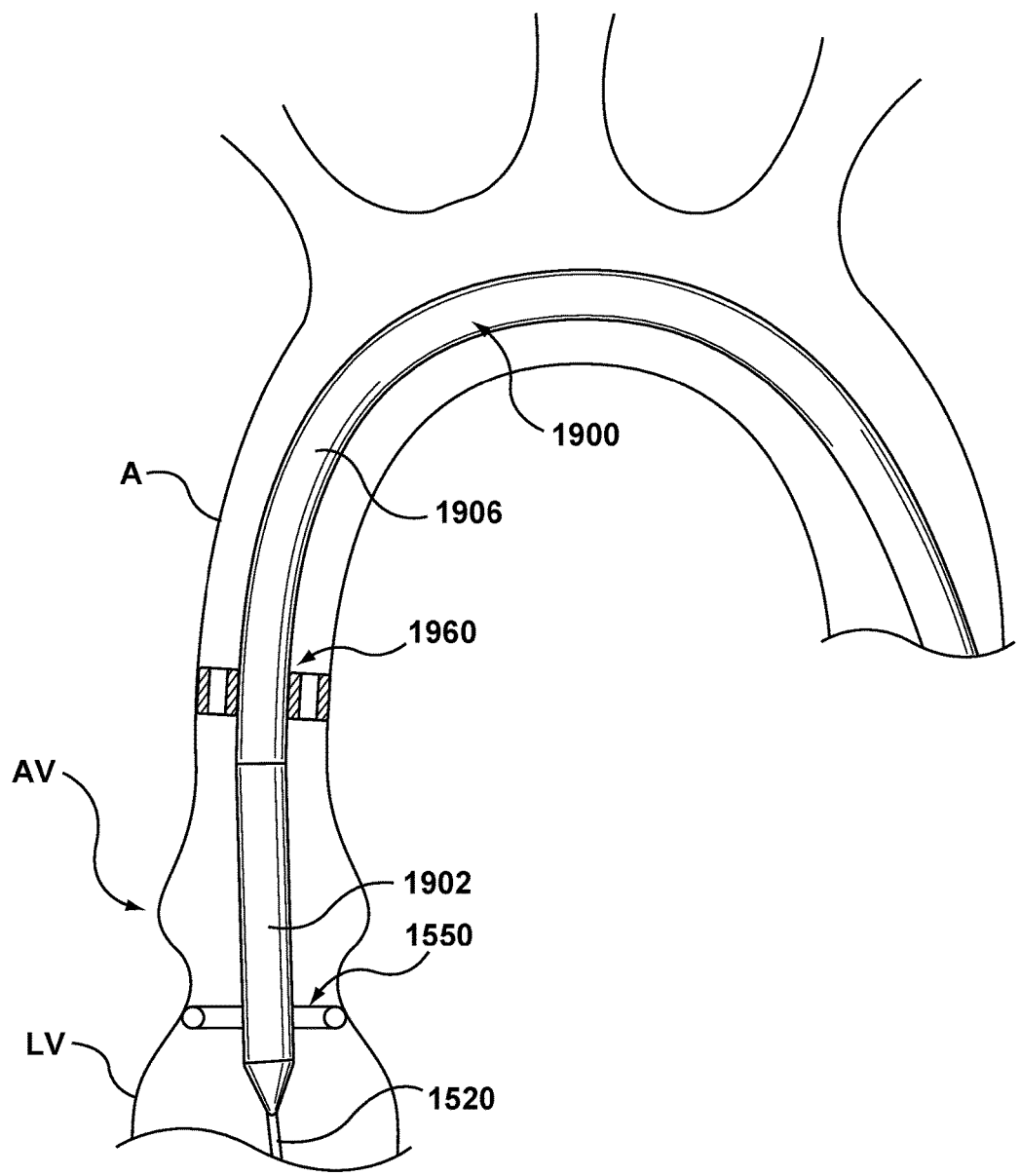
FIG. 19 is an illustration of a circumferential centering device of a valve delivery system in situ according to another embodiment hereof, wherein a longitudinal centering device of a valve centering catheter is in a deployed or expanded configuration, the circumferential centering device of the valve delivery system is in a deployed or expanded configuration, and a valve prosthesis of the valve delivery system is in a delivery or unexpanded configuration.

In another embodiment hereof, the circumferential centering device is integrated onto an outer shaft of the valve delivery system rather than a distal capsule section of the valve delivery system. More particularly, as shown on FIG. 19, valve delivery system 1900 includes a circumferential centering device 1960 proximal to the valve prosthesis. In the embodiment of FIG. 19, circumferential centering device 1960 is integrated onto an outer shaft 1906 of valve delivery system 1900. Similar to circumferential centering device 230, circumferential centering device 1960 is an annular inflatable balloon that has a tire-shaped or donut-shaped configuration defining a central opening or lumen (not shown in FIG. 19) there-through to allow for perfusion or blood flow during the valve replacement/repair procedure. At least a portion of circumferential centering device 1960 is sealingly attached to outer shaft 1906 of valve delivery system 1900, and outer shaft 1906 includes one or more ports (not shown) provide fluid communication between an inflation lumen (not shown) and an interior volume of circumferential centering device 1960. After valve delivery system 1900 is longitudinally positioned as desired, circumferential centering device 1960 of valve delivery system 1900 is radially expanded or inflated into an expanded configuration in order to circumferentially center valve delivery system 1900 and the valve prosthesis mounted thereon as shown in FIG. 19. Depending upon patient anatomy and the longitudinal location of circumferential centering device 1960 on outer shaft 1906, circumferential centering device 1960 may be positioned to deploy within the native valve annulus, proximal to the native valve annulus, within ascending aorta, and/or within the aortic arch. The valve prosthesis is then deployed into apposition with the native anatomy, thereby anchoring and securing the longitudinally and circumferentially centered position of the valve prosthesis within the native valve. In the embodiment of FIG. 19 in which circumferential centering device 1960 is integrated onto outer shaft 1906 of valve delivery system 1900, outer shaft 1906 and circumferential centering device 1960 remain stationary, with the circumferential centering device expanded and in contact with the native surrounding anatomy, during retraction of distal capsule section 1902 and deployment of the valve prosthesis.

Although the method described above with respect to FIGS. 15-19 includes concurrent use of a valve centering catheter having a longitudinal centering device thereon and a valve delivery system having a circumferential centering device thereon, the valve centering catheter(s) and the valve delivery system(s) described herein may be utilized separately or independent of each other. For example, valve centering catheter 1520 having longitudinal centering device 1550 thereon may be used with any valve delivery system such that the longitudinal centering device acts as a marker for depth control during delivery of the valve delivery system. In another example, valve delivery system 1700 having circumferential centering device 1760 integrated onto a distal capsule section thereof or valve delivery system 1900 having circumferential centering device 1960 integrated onto an outer shaft thereof may be tracked over a standard guidewire rather than valve centering catheter 1520, with the circumferential centering device being utilized to circumferentially center both the valve delivery system and the valve prosthesis within a native valve annulus prior to deployment of the valve prosthesis. In another example, circumferential centering device 1960 may be configured for use on a stand-alone or independent device or catheter rather than being integrated onto the outer shaft of valve delivery system 1900 as described above.

Figure 20:
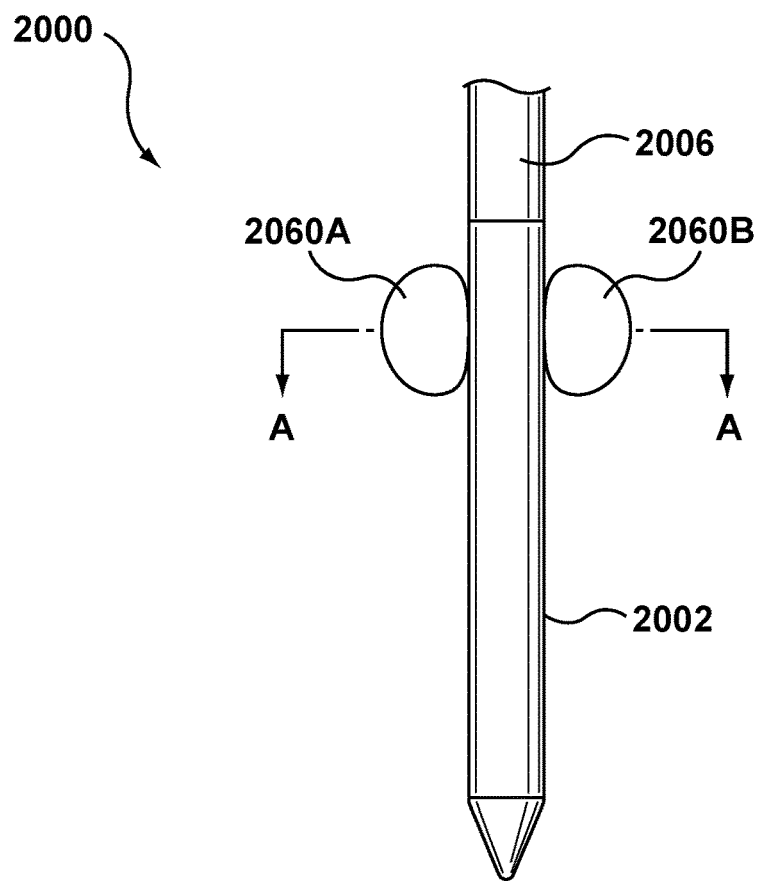
FIG. 20 is a side view of a distal portion of a valve delivery system that may be utilized in embodiment hereof, wherein the valve delivery system includes a plurality of eccentric centering devices or balloons in order to circumferentially center the valve delivery system.
Figure 20A:
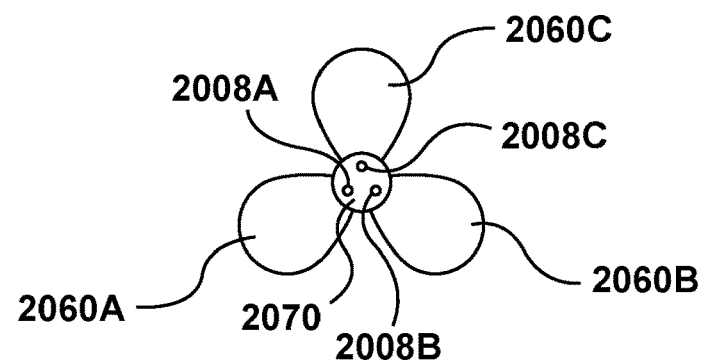
FIG. 20A is a cross-sectional view taken along line A-A of FIG. 20, wherein a multi-lumen shaft of the valve delivery system and the eccentric centering devices or balloons are removed from the valve delivery system for illustrative purposes only.

FIG. 20 illustrates a side view of a distal portion of a valve delivery system 2000 having a plurality of eccentric centering devices or balloons 2060A, 2060B, 2060C that may be used with valve centering catheter 1520 having longitudinal centering device 1550 thereon. More particularly, rather than having a circumferential centering device integrated onto a distal capsule section of the valve delivery system such as valve delivery system 1700, valve delivery system 2000 includes an outer shaft 2006 and an multi-lumen shaft 2070 (shown in FIG. 20A) that extends within outer shaft 2006 and defines a plurality of inflation lumens 2008A, 2008B, 2008C for delivery of inflation fluid to eccentric centering devices or balloons 2060A, 2060B, 2060C, respectively. In FIG. 20, valve delivery system 2000 is depicted with a valve prosthesis (not shown) in a delivery or compressed configuration in which the valve prosthesis is loaded within a distal capsule section 2002 of the delivery system and eccentric centering devices or balloons 2060A, 2060B, 2060C are shown in their inflated or expanded configurations. FIG. 20A illustrates a cross-sectional view taken along line A-A of FIG. 20 of multi-lumen shaft 2070 and eccentric centering devices or balloons 2060A, 2060B, 2060C removed from valve delivery system 2000 for illustrative purposes only. In an embodiment, only a single inflation port (not shown) is provided at a proximal end of valve delivery system 2000 to ensure uniform expansion of eccentric centering devices or balloons 2060A, 2060B, 2060C. In another embodiment, a plurality of inflation ports (not shown) are provided at a proximal end of valve delivery system 2000 so that eccentric centering devices or balloons 2060A, 2060B, 2060C may be individually inflated and adjusted as desired. Collectively, when expanded in situ, eccentric centering devices or balloons 2060A, 2060B, 2060C circumferentially center valve delivery system 2000 and the valve prosthesis mounted thereon with distal capsule 2002 while allowing for perfusion or blood flow during the valve replacement/repair procedure.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of delivering a valve prosthesis configured for delivery within a vasculature, the method comprising the steps of:

percutaneously introducing a valve centering catheter into a vasculature, the valve centering catheter having a circumferential centering device at a distal portion thereof, wherein the circumferential centering device is in a delivery configuration;

tracking the valve centering catheter through the vasculature until the circumferential centering device is positioned at a treatment site;

radially expanding the circumferential centering device into an expanded configuration at the treatment site, wherein the circumferential centering device has an outer wall and an inner wall with an interior space being defined between the outer wall and the inner wall, the inner wall defining a central opening there-through when in the expanded configuration;

percutaneously introducing a valve delivery system into the vasculature after the circumferential centering device has been radially expanded, the valve delivery system having a valve prosthesis at a distal portion thereof, wherein the valve prosthesis is in a delivery configuration;

tracking the valve delivery system through the vasculature until the valve prosthesis is positioned through the central opening of the expanded circumferential centering device in order to circumferentially center the valve prosthesis within the native anatomy of the treatment site; and deploying at least an inflow end of the valve prosthesis into apposition with the native anatomy of the treatment site while at least a portion of the valve prosthesis remains in the delivery configuration and positioned through the central opening of the expanded circumferential centering device, thereby anchoring and securing the circumferentially centered position of the valve prosthesis within the native anatomy of the treatment site.

2. The method of claim 1, further comprising the steps of:

radially collapsing the circumferential centering device after only the inflow end of the valve prosthesis is deployed;

removing the radially collapsed circumferential centering device from the treatment site, wherein an outflow end of the valve prosthesis remains in the delivery configuration during removal of the radially collapsed circumferential centering device; and deploying the outflow end of the valve prosthesis into apposition with the native anatomy of the treatment site after the removal of the circumferential centering device.

3. The method of claim 1, further comprising the steps of:

deploying an outflow end of the valve prosthesis into apposition with the native anatomy of the treatment site before the removal of the circumferential centering device;

radially collapsing the circumferential centering device after the outflow end of the valve prosthesis is deployed; and removing the radially collapsed circumferential centering device from the treatment site, wherein the radially collapsed circumferential centering device is of a sufficiently small profile so that the radially collapsed circumferential centering device slips past the deployed outflow end of the valve prosthesis without dislodging the valve prosthesis.

4. The method of claim 1, further comprising the steps of:

detaching the circumferential centering device from the valve centering catheter; and removing the valve centering catheter from the treatment site, wherein the circumferential centering device remains expanded around the valve prosthesis in situ after removal of the valve centering catheter.

5. The method of claim 4, wherein the step of radially expanding the circumferential centering device into an expanded configuration includes expanding the circumferential centering device with a self-expanding injectable substance.

6. The method of claim 1, wherein the circumferential centering device is an annular component such that the outer wall defines an outer periphery of the annular component and the inner wall defines an inner periphery of the annular component.

7. The method of claim 6, wherein the circumferential centering device is an inflatable balloon.

8. The method of claim 6, wherein the circumferential centering device is an expandable mesh component.

9. The method of claim 6, wherein the annular component includes a plurality of deformable regions that are configured to conform to the surrounding native anatomy.

10. The method of claim 9, wherein the annular component has a generally triangular cross-section and includes three vertices and three segments, the three vertices being the plurality of deformable regions, wherein the three vertices are formed with a first material that is more deformable than a second material of the three segments.

11. The method of claim 1, wherein the circumferential centering device has a C-shaped cross-section such that the outer wall is C-shaped and the inner wall is C-shaped.

12. The method of claim 11, wherein the circumferential centering device is an inflatable balloon.

13. The method of claim 12, wherein the step of percutaneously introducing a valve centering catheter into a vasculature includes introducing the valve centering catheter into a radial artery and the step of percutaneously introducing a valve delivery system into the vasculature includes introducing the valve delivery system into a femoral artery.

14. The method of claim 12, wherein ihe valve centering catheter includes a plurality of eccentric inflation ports.

15. A method of delivering a valve prosthesis configured for delivery within a vasculature, the method comprising the steps of:
percutaneously introducing a valve centering catheter into a vasculature, the valve centering catheter having a circumferential centering device at a distal portion thereof, wherein the circumferential centering device is in a delivery configuration;
tracking the valve centering catheter through the vasculature until the circumferential centering device is positioned at a treatment site;
radially expanding the circumferential centering device into an expanded configuration at the treatment site, wherein the circumferential centering device has an outer wall and an inner wall with an interior space being defined between the outer wall and the inner wall, the inner wall defining a central opening there-through when in the expanded configuration;
percutaneously introducing a valve delivery system into the vasculature, the valve delivery system being independent from the valve centering catheter, the valve delivery system having a valve prosthesis at a distal portion thereof, wherein the valve prosthesis is in a delivery configuration;
tracking the valve delivery system through the vasculature until the valve prosthesis is positioned through the central opening of the expanded circumferential centering device in order to circumferentially center the valve prosthesis within the native anatomy of the treatment site; and
deploying at least an inflow end of the valve prosthesis into apposition with the native anatomy of the treatment site while at least a portion of the valve prosthesis remains in the delivery configuration and positioned through the central opening of the expanded circumferential centering device, thereby anchoring and securing the circumferentially centered position of the valve prosthesis within the native anatomy of the treatment site.

16. The method of claim 15, further comprising the steps of:
radially collapsing the circumferential centering device after only the inflow end of the valve prosthesis is deployed;
removing the radially collapsed circumferential centering device from the treatment site, wherein an outflow end of the valve prosthesis remains in the delivery configuration during removal of the radially collapsed circumferential centering device; and
deploying the outflow end of the valve prosthesis into apposition with the native anatomy of the treatment site after the removal of the circumferential centering device.

17. The method of claim 15, further comprising the steps of:
deploying an outflow end of the valve prosthesis into apposition with the native anatomy of the treatment site before the removal of the circumferential centering device;
radially collapsing the circumferential centering device after the outflow end of the valve prosthesis is deployed; and
removing the radially collapsed circumferential centering device from the treatment site, wherein the radially collapsed circumferential centering device is of a sufficiently small profile so that the radially collapsed circumferential centering device slips past the deployed outflow end of the valve prosthesis without dislodging the valve prosthesis.

18. The method of claim 15, further comprising the steps of:
detaching the circumferential centering device from the valve centering catheter; and
removing the valve centering catheter from the treatment site, wherein the circumferential centering device remains expanded around the valve prosthesis in situ after removal of the valve centering catheter.

19. The method of claim 15, wherein the circumferential centering device is an annular component such that the outer wall defines an outer periphery of the annular component and the inner wall defines an inner periphery of the annular component.

20. The method of claim 19, wherein the annular component has a generally triangular cross-section and includes three vertices and three segments, the three vertices being formed with a first material that is more deformable than a second material of the three segments.

* * * * *